US008494829B2

(12) United States Patent
Teixeira

(10) Patent No.: US 8,494,829 B2
(45) Date of Patent: Jul. 23, 2013

(54) SENSOR FUSION AND PROBABILISTIC PARAMETER ESTIMATION METHOD AND APPARATUS

(76) Inventor: Rodrigo E. Teixeira, Madison, AL (US)

( * ) Notice: Subject to any disclaimer, the term of this patent is extended or adjusted under 35 U.S.C. 154(b) by 0 days.

(21) Appl. No.: 13/181,027

(22) Filed: Jul. 12, 2011

(65) Prior Publication Data

US 2012/0022350 A1    Jan. 26, 2012

Related U.S. Application Data

(60) Provisional application No. 61/366,437, filed on Jul. 21, 2010, provisional application No. 61/372,190, filed on Aug. 10, 2010, provisional application No. 61/373,809, filed on Aug. 14, 2010.

(51) Int. Cl.
 *G06F 17/18* (2006.01)
 *A61B 5/0205* (2006.01)
 *A61B 5/0402* (2006.01)

(52) U.S. Cl.
 USPC ................................ 703/11; 702/19; 600/324

(58) Field of Classification Search
 None
 See application file for complete search history.

(56) References Cited

U.S. PATENT DOCUMENTS

| | | | |
|---|---|---|---|
| 4,802,486 A * | 2/1989 | Goodman et al. ............ | 600/324 |
| 5,626,140 A * | 5/1997 | Feldman et al. .............. | 600/484 |
| 5,853,364 A | 12/1998 | Baker | |
| 6,405,108 B1 | 6/2002 | Patel | |
| 6,463,311 B1 | 10/2002 | Diab | |
| 6,505,145 B1 | 1/2003 | Bjornson | |
| 6,728,660 B2 | 4/2004 | Bjornson | |
| 6,882,959 B2 | 4/2005 | Rui | |
| 7,006,947 B2 | 2/2006 | Tryon | |
| 7,016,825 B1 | 3/2006 | Tryon, III et al. | |
| 7,018,338 B2 | 3/2006 | Vetter et al. | |
| 7,020,507 B2 | 3/2006 | Scharf | |
| 7,027,953 B2 | 4/2006 | Klein | |
| 7,058,550 B2 | 6/2006 | Kouritzin | |
| 7,079,888 B2 * | 7/2006 | Oung et al. .................. | 600/513 |
| 7,149,320 B2 | 12/2006 | Haykin | |
| 7,191,110 B1 | 3/2007 | Charbel | |
| 7,260,501 B2 | 8/2007 | Pattipatti | |
| 7,289,906 B2 | 10/2007 | Merwe | |
| 7,317,770 B2 | 1/2008 | Wang | |
| 7,480,601 B2 | 1/2009 | Tryon | |
| 7,536,277 B2 | 5/2009 | Pattipatti | |
| 2004/0122703 A1* | 6/2004 | Walker et al. ..................... | 705/2 |
| 2005/0113703 A1 | 5/2005 | Farringdon et al. | |
| 2005/0143634 A1* | 6/2005 | Baker et al. .................. | 600/310 |
| 2006/0166176 A1 | 7/2006 | Lakin | |
| 2006/0190217 A1 | 8/2006 | Lee | |
| 2008/0027341 A1 | 1/2008 | Sackner | |
| 2008/0082018 A1 | 4/2008 | Sackner | |
| 2009/0024332 A1 | 1/2009 | Karlov | |
| 2009/0069647 A1 | 3/2009 | McNames | |
| 2011/0077484 A1 | 3/2011 | Van Slyke et al. | |

FOREIGN PATENT DOCUMENTS
WO    WO 2008/055173 A2    5/2008

OTHER PUBLICATIONS

Singer et al. Pub Med PMID:3063772, abstract ( J Electrocardiol. 1988;21 Suppl:S46-S55).*
"Monitoring Metabolic Status: Predicting Decrements in Physiological and Cognitive Performance During Military", Apr. 2004, pp. 1-4, Report Brief, Institute of Medicine of the National Academies.
"Monitoring Metabolic Status: Predicting Decrements in Physiological and Cognitive Performance", 2004, pp. 1-33, Committee on Metabolic Monitoring for Military Field Applications, Standing Committee on Military Nutrition Research.
Arulampalam, Maskell, and Clapp, "A Tutorial on Particle Filters for Online Nonlinear/Non-Gaussian Bayesian Tracking", Feb. 2002, pp. 1-15, vol. 50, No. 2, IEEE Transactions on Signal Processing.
Bashi, Jiikov, Li, and Chen, "Distributed Implementations of Particle Filters", pp. 1-8.USA.
Boers and Driessen, "Particle Filter Track Before Detect Algorithms" Mar. 12, 2003, pp. 1-23, Thales.
Bokareva, Hu, Kanhere, Ristic, Gordon, Bessell, Rutten, and Jha, "Wireless Sensor Networks for Battlefield Surveillance", Oct. 2006, pp. 1-8, Land Warfare Conference.
Briegel and Tresp, "A Nonlinear State Space Model for the Blood Glucose Metabolism of a Diabetic", May 2002, pp. 228-236, Anwendungsaufsatz.
Chen, "Bayesian Filtering: From Kalman Filters to Particle Filters and Beyond", pp. 1-69.
Chen, Bakshi, Goel, and Ungarala, "Bayesian Estimation via Sequential Mote Carlo Sampling—Unconstrained Nonlinear Dynamic Systems", pp. 1-39.
Chen, Lee, Budhiraja, and Mehra, "PFLib—An Object Oriented MATLAB Toolbox for Particle Filtering", pp. 1-8.
Clifford and McSharry, "A Realistic Coupled Nonlinear Artificial ECG, BP, and Respiratory Signal Generator for Assessing Noise Performance of Biomedical Signal Processing Algorithms", pp. 1-12.
Clifford, "A Novel Framework for Signal Representation and Source Separation; Applications to Filtering and Segmentation of Biosignals", May 17, 2006. pp. 1-15. WSPC/Instruction File, Massachusetts, USA.

(Continued)

*Primary Examiner* — Michael Borin
(74) *Attorney, Agent, or Firm* — Kevin Hazen

(57) ABSTRACT

A probabilistic digital signal processor using data from multiple instruments is described. Initial probability distribution functions are input to a dynamic state-space model, which operates on state and/or model probability distribution functions to generate a prior probability distribution function, which is input to a probabilistic updater. The probabilistic updater integrates sensor data from multiple instruments with the prior to generate a posterior probability distribution function passed (1) to a probabilistic sampler, which estimates one or more parameters using the posterior, which is output or re-sampled in an iterative algorithm or (2) iteratively to the dynamic state-space model. For example, the probabilistic processor operates on fused data using a physical model, where the data originates from a mechanical system or a medical meter or instrument, such as an electrocardiogram or pulse oximeter to generate new parameter information and/or enhanced parameter information.

8 Claims, 22 Drawing Sheets

OTHER PUBLICATIONS

Clifford, Shoeb, McSharry, and Janz, "Model-Based Filtering, Compression and Classification of the ECG", pp. 1-4.

Crisan and Doucet, "A Survey of Convergence Results on Particle Filtering Methods for Practitioners", Mar. 2002, pp. 1-11, vol. 50, No. 3, IEEE Transactions on Signal Processing.

Dawant, Uckun, Manders, and Lindstrom, "Model-Based Signal Acquisition, Analysis, and Interpretation in Intelligent Patient Monitoring", Dec. 1993, pp. 82-92, IEEE Engineering in Medicine and Biology.

Doucet, Freitas, Murphy, and Russell, "Rao-Blackwellised Particle Filtering for Dynamic Bayesian Networks", pp. 1-8.

Dripps, "An Introduction to Model Based Digital Signal Processing", pp. 1-4.

Feuerstein, Parker, and Bouotelle, "Practical Methods for Noise Removal: Applications to Spikes, Nonstationary Quasi-Periodic Noise, and Baseline Drift", May 18, 2009, pp. 1-20, American Chemical Society.

Ford, "Non-Linear and Robust Filtering: From the Kalman Filter to the Particle Filter", Apr. 2002, pp. 1-53, DSTO Aeronautical I and Maritime Research Laboratory, Australia.

Goebel, "Pronostics", Apr. 27, 2010, pp. 1-47, NASA Ames Research Center, Moffett Field, CA.

Hall and Llinas, "An Introduction to Multisensor Data Fusion", Jan. 1997, pp. 1-18, vol. 85, No. 1, Proceedings of the IEEE.

Han, Kim, and Kim, "Development of Real-Time Motion Artifact Reduction Algorithm for a Wearable Photoplethysmography", pp. 1-4, Aug. 23, 2007, Proceedings of the 29$^{th}$ Annual International Conference of the IEEE EMBS, Lyon, France.

Hoyt, "SPARNET—Spartan Sensor Network to Improve Medical and Situational Awareness of Foot Soldiers During Field Training", Jan. 9, 2007, pp. 1-2, U.S. Army Research Institute of Environmental Medicine. MA.

Hsiao, Plinval-Salgues, and Miller, "Particle Filters and Their Applications", Apr. 11, 2005, pp. 1-99, Cognitive Robotics.

Huang and Wang, "Overview of Emerging Bayesian Approach to Nonlinear System Identification", Apr. 6, 2006, pp. 1-12, International Workshop on Solving Industrial Control and Optimization Problems, Cramado, Brazil.

Hutter and Dearden, "The Gaussian Particle Filter for Diagnosis of Non-Linear Systems", pp. 1-6, Tecnische Universitat Darmstadt, NASA Ames Research Center. CA.

Isermann, "Model-Based Fault-Detection and Diagnosis—Status and Applications", pp. 71-85, Annual Reviews in Control.

Johansen, Doucet, and Davy, "Particle Methods for Maximum Likelihood Estimation in Latent Variable Models", Aug. 31, 2007, pp. 1-11, Springer.

Kantas, Doucet, Singh, and Maciejowski, "An Overview of Sequential Monte Carlo Methods for Parameter Estimation in General State-Space Models", pp. 1-19.

Kueck and Freitas, "Where Do Priors and Causal Models Come From? An Experimental Design Perspective", Apr. 7, 2010, pp. 1-13, University of British Columbia, Technical Report.

Lee, "A Particle Algorithm for Sequential Bayesian Parameter Estimation and Model Selection", Feb. 2, 2002. pp. 1-11, vol. 50, No. 2, IEEE Transactions on Signal Processing.

Maybeck, "Stochastic Models, Estimation, and Control", pp. 1-19, vol. 1, Academic Press.

McSharry and Clifford, "Open-Source Software for Generating Electrocardiogram Signals", Jun. 4, 2004, pp. 1-10, Psys.Med.Biol.

Merwe and Wan, "Gaussian Mixture Sigma-Point Particle Filters for Sequential Probabilistic Inference in Dynamic State-Space Models", pp. 1-4.

Merwe and Wan, "Sigma-Point Kalman Filters for Probabilistic Inference in Dynamic State-Space Models", pp. 1-27, OGI School of Science and Engineering, Oregon Health and Science University, Oregon, USA.

Merwe and Wan, "The Square-Root Unscented Kalman Filter for State and Parameter-Estimation" pp. 1-4, Oregon Graduate Institute of Science and Technology. Oregon, USA.

Merwe, "Sigma-Point Kalman Filters for Probabilistic Inference in Dynamic State-Space Models", Apr. 2004, pp. 1-397, Oregon Health and Science University. Oregon.

Merwe, Doucet, Freitas, and Wan, "The Unscented Particle Filter", Aug. 16, 2000, pp. 1-46, Cambridge University Engineering Department, Technical Report.

Merwe, Julier, and Wan, "Sigma-Point Kalman Filters for Nonlinear Estimation and Sensor-Fusion-Application to Integrated Navigation", pp. 1-30, American Institute of Aeronautics and Astronautics.

Morales-Menendez, Freitas, and Poole, "Real-Time Monitoring of Complex Industrial Processes with Particle Filters", pp. 1-8.

Niethammer, "Introduction to Estimation Theory", pp. 1-49, Department of Computer Science University of North Carolina.

Norris, Suwanmongkol, Geissbuhler, and Dawant, "The SIMON Architecture: Distributing Data, Tasks, and Knowledge in Intelligent ICU Monitoring Systems", pp. 1-10, Vanderbilt University, Tennessee.

Oreshkin and Coates, "Bootstrapping Particle Filters using Kernel Recursive Least Squares", pp. 1-7, Department of Electrical and Computer Engineering, Canada.

Parker, "A Model-Based Algorithm for Blood Glucose Control in Type I Diabetic Patients", Feb. 1999, pp. 1-10, vol. 46, No. 2, IEEE Transactions on Biomedical Engineering.

Rasmussen and Ghahramani, "Bayesian Monte Carlo", pp. 1-8, Gatsby Computational Neuroscience Unit, London, England.

Sameni, "A Nonlinear Bayesian Filtering Framework for ECG Denoising", vol. XX, No. YY, pp. 1-14, IEEE Transactions on Biomedical Engineering.

Sameni, "A Nonlinear Bayesian Filtering Framework for the Filtering of Noisy ECG Signals", Apr. 21, 2006, pp. 1-62, Laboratoire des Images et des Signaux, France.

Sameni, Shamsollahi, and Jutten, Muti-Channel Electrocardiogram Denoising Using a Bayesian Filtering Framework, 2006. pp. 1-4, Computer in Cardiology.

Sameni, Shamsollahi, Jutten, and Zadeh, "Filtering Noisy ECG Signals Using the Extended Kalman Filter Based on a Modified Dynamic ECG Model" pp. 1-4.

Storvik, "Particle Filters for State-Space Models With the Presence of Unknown Static Parameters", Feb. 2002, pp. 281-289, vol. 50, No. 2, IEEE Transactions on Signal Processing.

Thrun, "Particle Filters in Robotics or: How the World Became to Be One Big Bayes Network" Aug. 2, 2002, pp. 1-74, UAI.

Thrun, "Stanley: The Robot That Won The DARPA Grand Challenge", pp. 1-41, Stanford Artificial Intelligence Laboratory, CA.

Verma, Thrun, and Simmons, "Variable Resolution Particle Filter", Aug. 2003, pp. 1-6, In Proceedings of the International Joint Conference on Artificial Intelligence.

Wan, Merwe, and Nelson, "Dual Estimation and the Unscented Transformation", pp. 1-7, Oregon Graduate Institute of Science and Technology Department of Electrical and Computer Engineering, Portland, Oregon.

Wegman, Leuenberger, Neuenschwander, and Excoffier, "ABCtoolbox: A Versatile toolkit for Approximate Bayesian Computations", Mar. 4, 2010, BMC Bioinformatics.

Welch and Biship, "An Introduction to the Kalman Filter", Jul. 24, 2006, pp. 1-16, Department of Computer Science University of North Carolina, NC.

Welch and Bishop, "An Introduction to the Kalman Filter", pp. 1-80. Association for Computing Machinery.

Welch, "Team18: The Kalman Filter Learning Tool Dynamic and Measurement Models", Feb. 17, 2003, pp. 1-11, University of North Carolina. NC.

Wu, Rangaraj, Rangayyan, and Ng, "Cancellation of Artifacts in ECG Signals Using a Normalized Adaptive Neural Filter", pp. 1-4, Aug. 23, 2007, Proceedings of the 29$^{th}$ Annual International Conference of the IEEE EMBS, Lyon, France.

Xu and Li, "Rao-Blackwellised Particle Filter for Tracking with Application in Visual Surveillance", pp. 1-8, Department of Computer Science and Engineering Arizona State University, AZ.

Arulampalam et al. IEEE Transactions on Signal Processing, vol. 50, No. 2, 2002, 174-187.

Wukitsch et al., Journal of Clinical Monitoring, vol. 4, pp. 290-301, 1998.

* cited by examiner

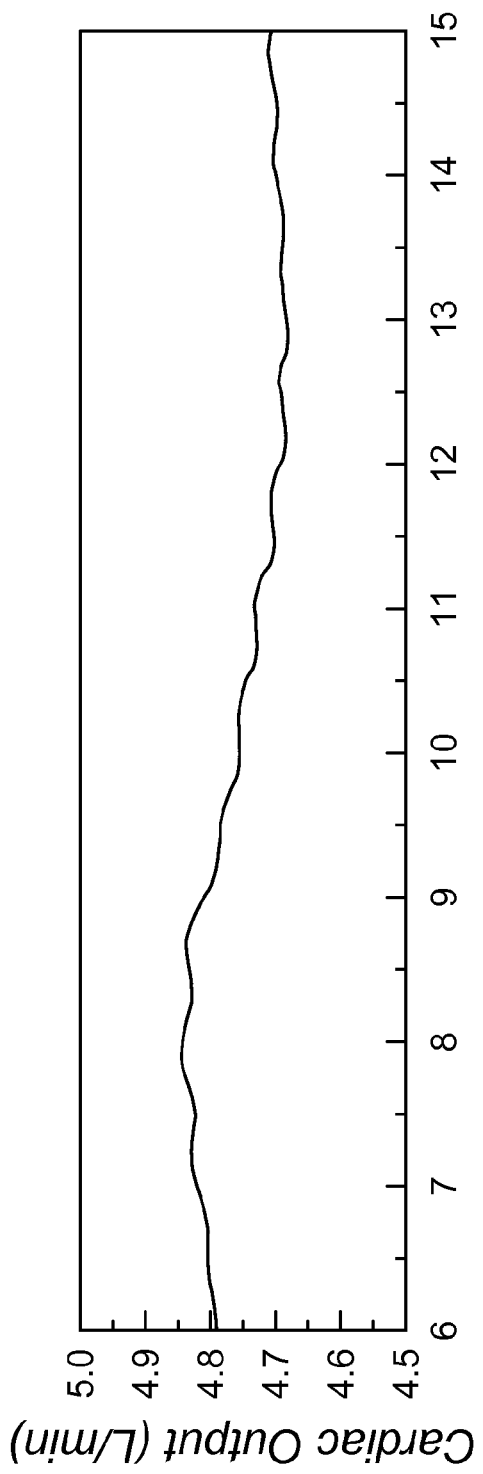
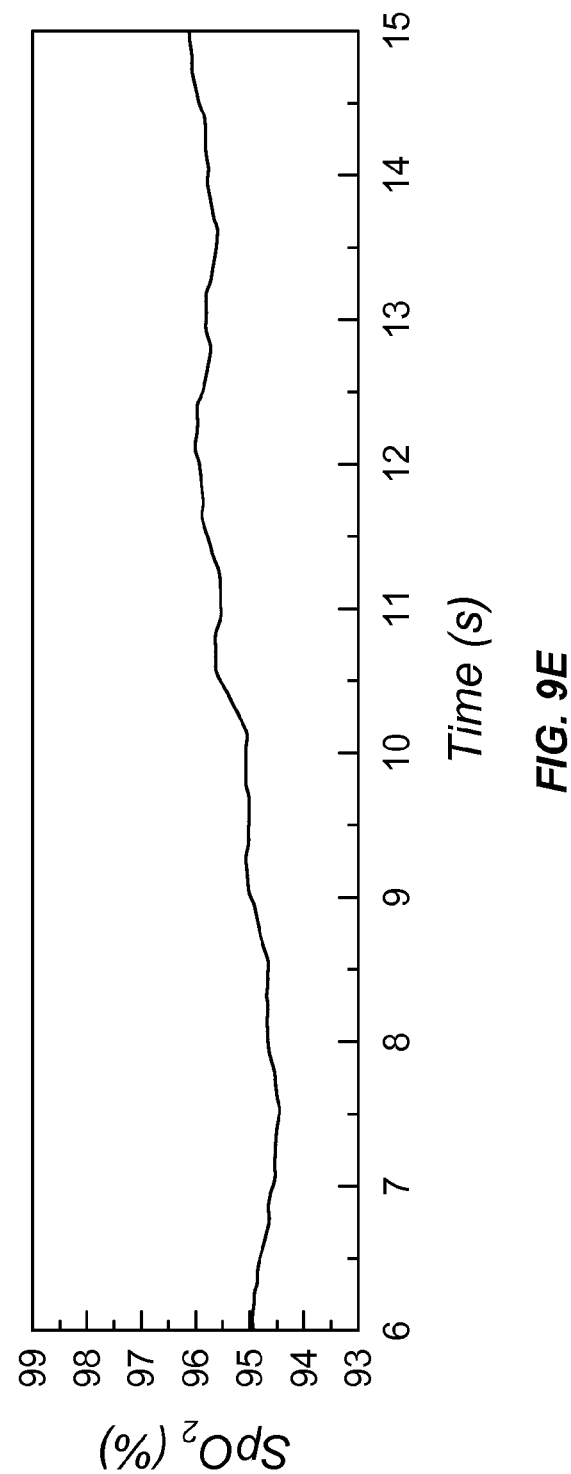
FIG. 9D
FIG. 9E

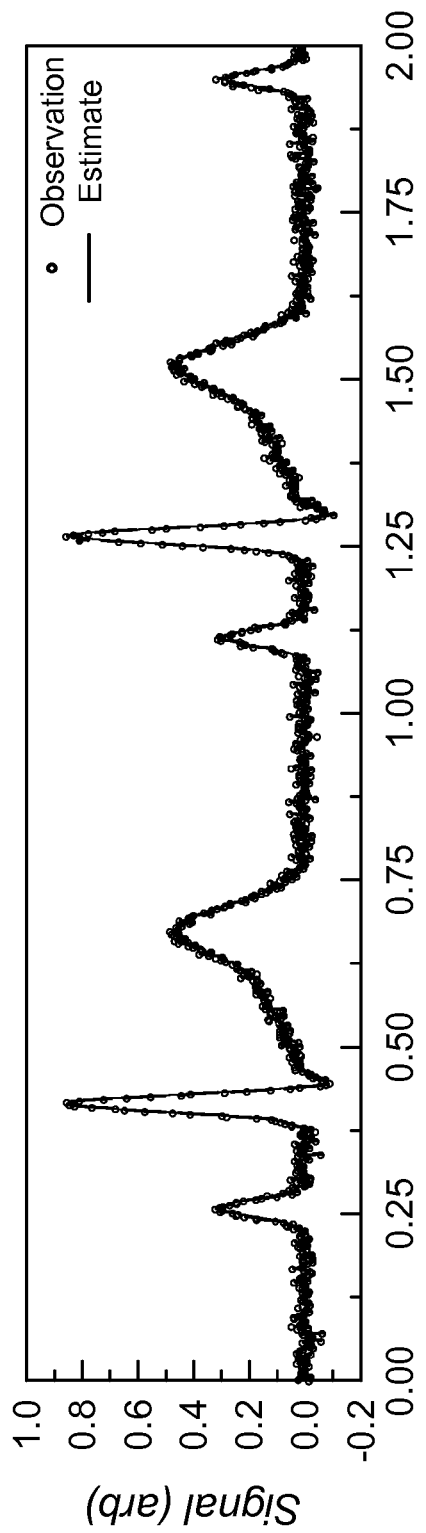
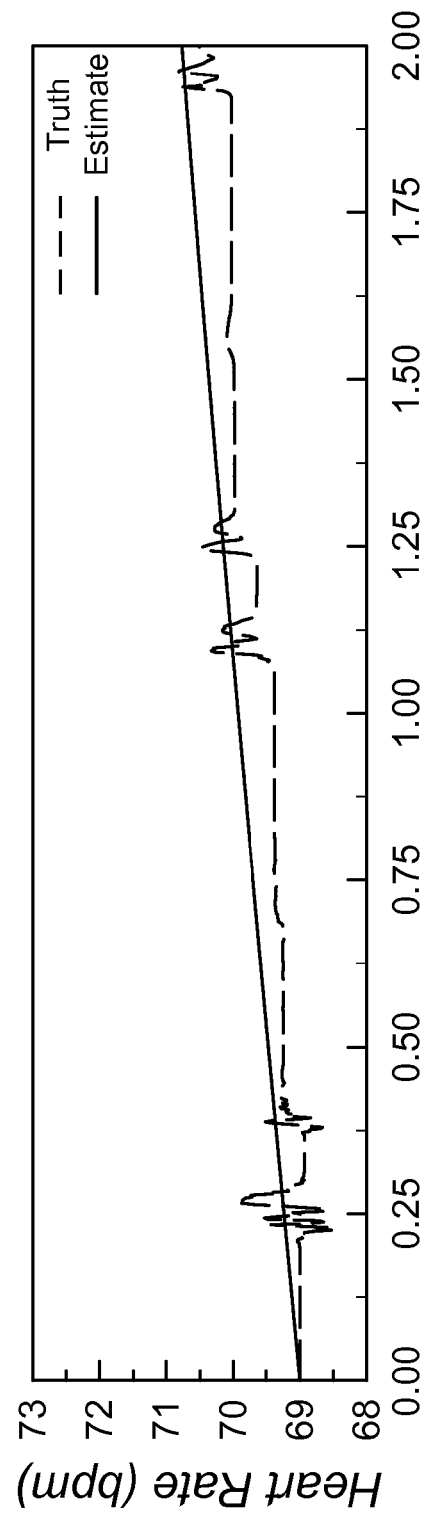
FIG. 12A
FIG. 12B

SENSOR FUSION AND PROBABILISTIC PARAMETER ESTIMATION METHOD AND APPARATUS

CROSS-REFERENCES TO RELATED APPLICATIONS

This application claims:
priority to U.S. patent application Ser. No. 12/796,512, filed Jun. 8, 2010, which claims priority to U.S. patent application Ser. No. 12/640,278, filed Dec. 17, 2009, which under 25 U.S.C. 120 claims benefit of U.S. provisional patent application No. 61/171,802, filed Apr. 22, 2009;
benefit of U.S. provisional patent application No. 61/366,437 filed Jul. 21, 2010;
benefit of U.S. provisional patent application No. 61/372,190 filed Aug. 10, 2010; and
benefit of U.S. provisional patent application No. 61/373,809 filed Aug. 14, 2010,
all of which are incorporated herein in their entirety by this reference thereto.

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

BACKGROUND OF THE INVENTION

1. Field of the Invention

The present invention relates generally to apparatus and methods for processing and/or representing sensor data, such as mechanical or medical sensor data.

2. Discussion of the Related Art

Mechanical devices and biomedical monitoring devices such as pulse oximeters, glucose sensors, electrocardiograms, capnometers, fetal monitors, electromyograms, electroencephalograms, and ultrasounds are sensitive to noise and artifacts. Typical sources of noise and artifacts include baseline wander, electrode-motion artifacts, physiological artifacts, high-frequency noise, and external interference. Some artifacts can resemble real processes, such as ectopic beats, and cannot be removed reliably by simple filters; however, these are removable by the techniques taught herein. In addition, mechanical devices and biomedical monitoring devices address a limited number of parameters. It would be desirable to expand the number of parameters measured, such as to additional biomedical state parameters.

Patents related to the current invention are summarized herein.

Mechanical Systems

Several reports of diagnostics and prognostics applied to mechanical systems have been reported.

Vibrational Analysis

R. Klein "Method and System for Diagnostics and Prognostics of a Mechanical System", U.S. Pat. No. 7,027,953 B2 (Apr. 11, 2006) describes a vibrational analysis system for diagnosis of health of a mechanical system by reference to vibration signature data from multiple domains, which aggregates several features applicable to a desired fault for trend analysis of the health of the mechanical system.

Intelligent System

S. Patel, et. al. "Process and System for Developing Predictive Diagnostic Algorithms in a Machine", U.S. Pat. No. 6,405,108 B1 (Jun. 11, 2002) describe a process for developing an algorithm for predicting failures in a system, such as a locomotive, comprising conducting a failure mode analysis to identify a subsystem, collecting expert data on the subsystem, and generating a predicting signal for identifying failure modes, where the system uses external variables that affect the predictive accuracy of the system.

C. Bjornson, "Apparatus and Method for Monitoring and Maintaining Plant Equipment", U.S. Pat. No. 6,505,145 B1 (Jan. 11, 2003) describes a computer system that implements a process for gathering, synthesizing, and analyzing data related to a pump and/or a seal, in which data are gathered, the data is synthesized and analyzed, a root cause is determined, and the system suggests a corrective action.

C. Bjornson, "Apparatus and Method for Monitoring and Maintaining Plant Equipment", U.S. Pat. No. 6,728,660 B2 (Apr. 27, 2004) describes a computer system that implements a process for gathering, synthesizing, and analyzing data related to a pump and/or a seal, in which data are gathered, the data is synthesized and analyzed, and a root cause is determined to allow a non-specialist to properly identify and diagnose a failure associated with a mechanical seal and pump.

K. Pattipatti, et. al. "Intelligent Model-Based Diagnostics for System Monitoring, Diagnosis and Maintenance", U.S. Pat. No. 7,536,277 B2 (May 19, 2009) and K. Pattipatti, et. al. "Intelligent Model-Based Diagnostics for System Monitoring, Diagnosis and Maintenance", U.S. Pat. No. 7,260,501 B2 (Aug. 21, 2007) both describe systems and methods for monitoring, diagnosing, and for condition-based maintenance of a mechanical system, where model-based diagnostic methodologies combine or integrate analytical models and graph-based dependency models to enhance diagnostic performance.

Inferred Data

R. Tryon, et. al. "Method and Apparatus for Predicting Failure in a System", U.S. Pat. No. 7,006,947 B2 (Feb. 28, 2006) describe a method and apparatus for predicting system failure or reliability using a computer implemented model relying on probabilistic analysis, where the model uses data obtained from references and data inferred from acquired data. More specifically, the method and apparatus uses a pre-selected probabilistic model operating on a specific load to the system while the system is under operation.

Virtual Prototyping

R. Tryon, et. al. "Method and Apparatus for Predicting Failure of a Component", U.S. Pat. No. 7,016,825 B1 (Mar. 21, 2006) describe a method and apparatus for predicting component failure using a probabilistic model of a material's microstructural-based response to fatigue using virtual prototyping, where the virtual prototyping simulates grain size, grain orientation, and micro-applied stress in fatigue of the component.

R. Tryon, et. al. "Method and Apparatus for Predicting Failure of a Component, and for Determining a Grain Orientation Factor for a Material", U.S. Pat. No. 7,480,601 B2 (Jan. 20, 2009) describe a method and apparatus for predicting component failure using a probabilistic model of a material's microstructural-based response to fatigue using a computer simulation of multiple incarnations of real material behavior or virtual prototyping.

Medical Systems

Several reports of systems applied to biomedical systems have been reported.

Lung Volume

M. Sackner, et. al. "Systems and Methods for Respiratory Event Detection", U.S. Patent application no. 2008/0082018 A1 (Apr. 3, 2008) describe a system and method of processing respiratory signals from inductive plethysmographic sensors in an ambulatory setting that filters for artifact rejection to improve calibration of sensor data and to produce output indicative of lung volume.

Pulse Oximeter

J. Scharf, et. al. "Separating Motion from Cardiac Signals Using Second Order Derivative of the Photo-Plethysmograph and Fast Fourier Transforms", U.S. Pat. No. 7,020,507 B2 (Mar. 28, 2006) describes the use of filtering photo-plethysmograph data in the time domain to remove motion artifacts.

M. Diab, et. al. "Plethysmograph Pulse Recognition Processor", U.S. Pat. No. 6,463,311 B1 (Oct. 8, 2002) describe an intelligent, rule-based processor for recognition of individual pulses in a pulse oximeter-derived photo-plethysmograph waveform operating using a first phase to detect candidate pulses and a second phase applying a plethysmograph model to the candidate pulses resulting in period and signal strength of each pulse along with pulse density.

C. Baker, et. al. "Method and Apparatus for Estimating Physiological Parameters Using Model-Based Adaptive Filtering", U.S. Pat. No. 5,853,364 (Dec. 29, 1998) describe a method and apparatus for processing pulse oximeter data taking into account physical limitations using mathematical models to estimate physiological parameters.

Cardiac

J. McNames, et. al. "Method, System, and Apparatus for Cardiovascular Signal Analysis, Modeling, and Monitoring", U.S. patent application publication no. 2009/0069647 A1 (Mar. 12, 2009) describe a method and apparatus to monitor arterial blood pressure, pulse oximetry, and intracranial pressure to yield heart rate, respiratory rate, and pulse pressure variation using a statistical state-space model of cardiovascular signals and a generalized Kalman filter to simultaneously estimate and track the cardiovascular parameters of interest.

M. Sackner, et. al. "Method and System for Extracting Cardiac Parameters from Plethysmograph Signals", U.S. patent application publication no. 2008/0027341 A1 (Jan. 31, 2008) describe a method and system for extracting cardiac parameters from ambulatory plethysmographic signal to determine ventricular wall motion.

Hemorrhage

P. Cox, et. al. "Methods and Systems for Non-Invasive Internal Hemorrhage Detection", International Publication no. WO 2008/055173 A2 (May 8, 2008) describe a method and system for detecting internal hemorrhaging using a probabilistic network operating on data from an electrocardiogram, a photoplethysmogram, and oxygen, respiratory, skin temperature, and blood pressure measurements to determine if the person has internal hemorrhaging.

Disease Detection

V. Karlov, et. al. "Diagnosing Inapparent Diseases From Common Clinical Tests Using Bayesian Analysis", U.S. patent application publication no. 2009/0024332 A1 (Jan. 22, 2009) describe a system and method of diagnosing or screening for diseases using a Bayesian probability estimation technique on a database of clinical data.

STATEMENT OF THE PROBLEM

Mechanical and biomedical sensors are typically influenced by multiple sources of contaminating signals that often overlap the frequency of the signal of interest, making it difficult, if not impossible, to apply conventional filtering. Severe artifacts such as occasional signal dropouts due to sensor movement or large periodic artifacts are also difficult to filter in real time. Biological sensor hardware can be equipped with a computer comprising software for post-processing data and reducing or rejecting noise and artifacts. Current filtering techniques typically use some knowledge of the expected frequencies of interest where the sought-after physiological information should be found.

Adaptive filtering has been used to attenuate artifacts in pulse oximeter signals corrupted with overlapping frequency noise bands by estimating the magnitude of noise caused by patient motion and other artifacts and canceling its contribution from pulse oximeter signals during patient movement. Such a time correlation method relies on a series of assumptions and approximations to the expected signal, noise, and artifact spectra, which compromises accuracy, reliability, and general applicability.

Filtering techniques based on Kalman and extended Kalman techniques offer advantages over conventional methods and work well for filtering linear systems or systems with small nonlinearities and Gaussian noise. These filters, however, are not adequate for filtering highly nonlinear systems and non-Gaussian/non-stationary noise. Therefore, obtaining reliable biomedical signals continue to present problems, particularly when measurements are made in mobile, ambulatory, and physically active patients.

Existing data processing techniques, including adaptive noise cancellation filters, are unable to extract information that is hidden or embedded in biomedical signals and also discard some potentially valuable information.

Existing medical sensors sense a narrow spectrum of medical parameters and states. What is needed is a system readily expanding the number of biomedical states determined.

A method or apparatus for extracting additional useful information from a mechanical sensor in a mechanical system, a biomedical system, and/or a system component or sub-component is needed to provide users additional and/or clearer information.

SUMMARY OF THE INVENTION

The invention comprises use of fused data in a probabilistic model to extract, filter, estimate and/or add additional information about a system based on data from a sensor.

DESCRIPTION OF THE FIGURES

A more complete understanding of the present invention is derived by referring to the detailed description and claims when considered in connection with the Figures, wherein like reference numbers refer to similar items throughout the Figures.

FIG. 12 is a chart showing noisy non-stationary ECG sensor data input, FIG. 12A and FIG. 12B and processed heart rate and ECG output, FIG. 12A and FIG. 12B, for a data processor configured to process ECG sensor data;

DETAILED DESCRIPTION OF THE INVENTION

Figure 1:
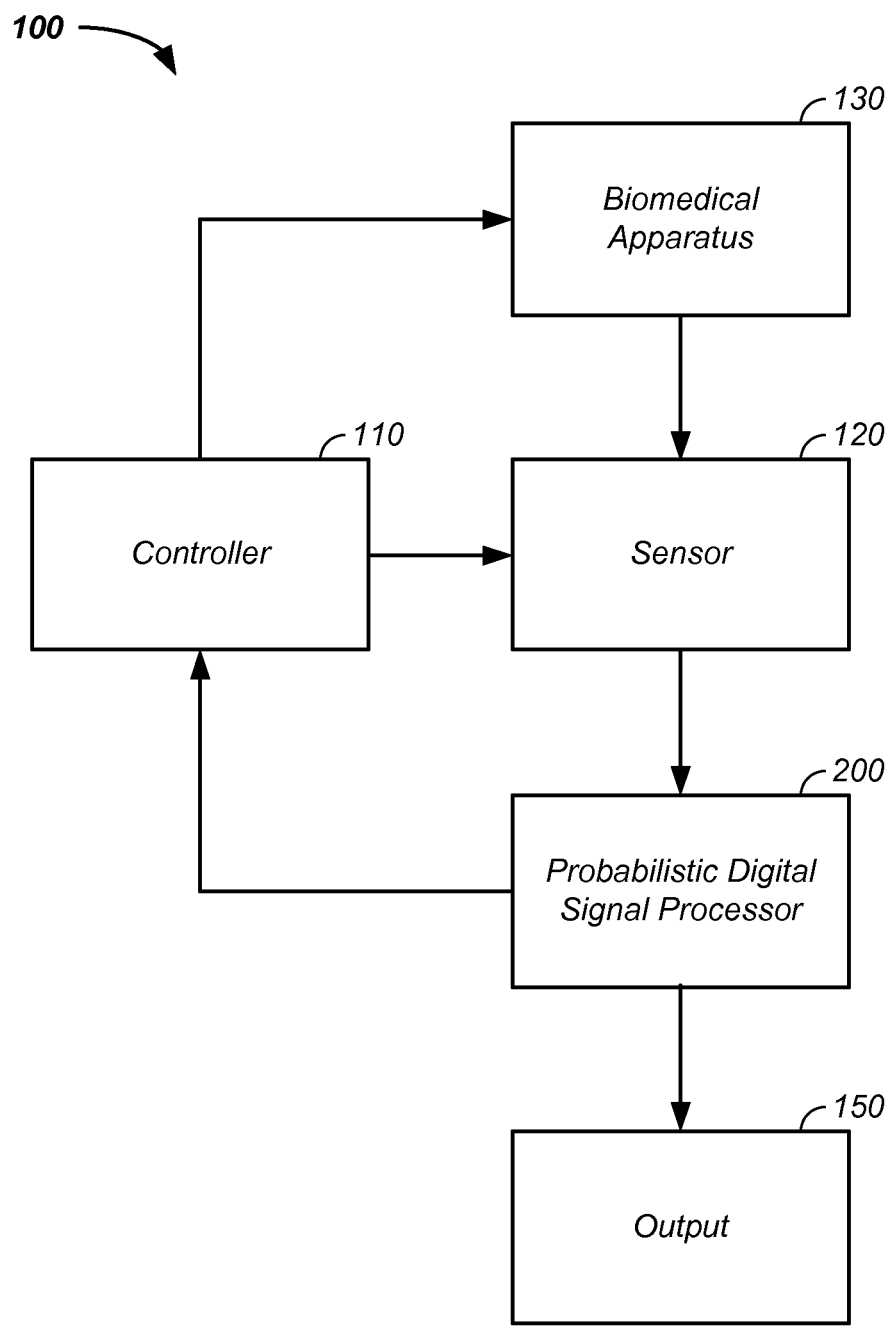
FIG. 1 illustrates operation of the intelligent data extraction algorithm on a biomedical apparatus.

The invention comprises use of a method, a system, and/or an apparatus using a probabilistic model for monitoring and/or estimating a parameter using fused data from multiple sensors.

The system applies to the mechanical and medical fields. Herein, for clarity the system is applied to biomedical devices, though the system concepts apply to mechanical apparatus.

In one embodiment, an intelligent data extraction algorithm (IDEA) is used in a system, which combines a dynamic state-space model with a probabilistic digital signal processor to estimate a parameter, such as a biomedical parameter. Initial probability distribution functions are input to a dynamic state-space model, which iteratively operates on probability distribution functions (PDFs), such as state and model probability distribution functions, to generate a prior probability distribution function, which is input into a probabilistic updater. The probabilistic updater integrates sensor data with the prior probability distribution function to generate a posterior probability distribution function passed to a probabilistic sampler, which estimates one or more parameters using the posterior, which is output or re-sampled and used as an input to the dynamic state-space model in the iterative algorithm. In various embodiments, the probabilistic data signal processor is used to filter output and/or estimate a value of a new physiological parameter from a biomedical device using appropriate physical models, which optionally include biomedical, chemical, electrical, optical, mechanical, and/or fluid based models. For clarity, examples of heart and cardiovascular medical devices are provided.

In one example, an analyzer is configured for processing sensor data representative of a body where the analyzer includes: a physical model representative of function of a body constituent; the physical model coded into a digital signal processor electrically connected to a computer embedded in the analyzer. The digital signal processor is configured to: (1) generate a prior probability distribution function using the physical model and (2) repetitively fuse input data originating from at least two types of medical instruments with the prior probability distribution function to generate a posterior probability distribution function. Further, the processor is configured to process the posterior probability distribution function to generate an output of at least one of: (1) a monitored parameter value representative of the body and (2) an estimated parameter value representative of the body.

In various embodiments, the probabilistic digital signal processor comprises one or more of a dynamic state-space model, a dual or joint updater, and/or a probabilistic sampler, which process input data, such as sensor data and generates an output. Preferably, the probabilistic digital signal processor (1) iteratively processes the data and/or (2) uses a mathematical model of the physical system in processing the input data.

The probabilistic digital signal processor optionally:
- operates on or in conjunction with a sensor in a mechanical system;
- filters input data;
- operates using data from a medical meter, where the medical meter yields a first physical parameter from raw data, to generate a second physical parameter not output by the medical meter;
- operates on discrete/non-probabilistic input data, such as from a mechanical device or a medical device to generate a probabilistic output function;
- iteratively circulates or dynamically circulates a probability distribution function through at least two of the dynamic state-space model, the dual or joint updater, and/or the probabilistic sampler;
- fuses or combines output from multiple sensors, such as two or more medical devices; and
- prognosticates probability of future events.

To facilitate description of the probabilistic digital signal processor, a non-limiting example of a hemodynamics process model is provided. In this example, the probabilistic digital signal processor is provided:
- raw sensor data, such as current, voltage, and/or resistance; and/or
- output from a medical device to a first physical or chemical parameter.

In this example, the medical device is a pulse oximeter and the first parameter from the pulse oximeter provided as input to the probabilistic digital signal processor is one or more of:
- raw data, such as a voltage, waveform, and/or an intensity;
- heart rate; and/or
- blood oxygen saturation.

The probabilistic digital signal processor uses a physical model, such as a probabilistic model, to operate on the first physical parameter to generate a second physical parameter, where the second physical parameter is not the first physical parameter. For example, the output of the probabilistic digital signal processor when provided with the pulse oximeter data is one or more of:
- a heart stroke volume;
- a cardiac output flow rate;
- an aortic blood pressure; and/or
- a radial blood pressure.

Optionally, the output from the probabilistic model is an updated, an error filtered, and/or a smoothed version of the original input data, such as a smoothed blood oxygen saturation percentage as a function of time. The hemodynamics model is further described, infra.

To facilitate description of the probabilistic digital signal processor, another non-limiting example of an electrocardiograph process model is provided. In this example, the probabilistic digital signal processor is provided:
- raw sensor data, such as intensity, an electrical current, and/or a voltage; and/or output from a medical device, such as an electrocardiogram, to a first physical or electrical parameter.

In this example, the medical device is a electrocardiograph and the first physical or electrical parameter from the electrocardiograph system provided as input to the probabilistic digital signal processor is one or more of:
- raw data; and/or
- an electrocardiogram.

The probabilistic digital signal processor uses a physical model, such as a probabilistic model, to operate on the first physical parameter to generate a second physical parameter or an indicator, where the second physical parameter is not the first physical parameter. For example, the output of the probabilistic digital signal processor when provided with the electrocardiogram or raw data is one or more of:
- an arrhythmia detection;
- an ischemia warning; and/or
- a heart attack prediction.

Optionally, the output from the probabilistic model is an updated, error filtered, or smoothed version of the original input data. For example, the probabilistic processor uses a physical model where the output of the model processes low signal-to-noise ratio events to yield an early warning of any of the arrhythmia detection, the ischemia warning, and/or the heart attack prediction. The electrocardiograph model is further described, infra.

To still further facilitate description of the probabilistic digital signal processor, non-limiting fusion examples are provided, which combine data from one or more of:
- a mechanical system;
- a sensor monitoring a mechanical device;
- an electrodynamics based medical device;
- a hemodynamic based medical device;
- accelerometer data; and
- an environmental meter.

As further described, supra, fusion of signals or sensor data from a plurality of devices allows:
- detection of a false positive or false negative signal from a first device with a second device;
- noise recognized in first sensor data as the noise is not present in a second sensor type or is correlated with noise of the second sensor type;
- fusion of environmental data with medical data;
- determination of an additional parameter not independently measured with individual data types of the fused data;
- electrocardiograph data to aid in analysis of pulse oximeter data and vise-versa; and/or
- electrodynamic information to aid in analysis of hemodynamic information and vise-versa.

Deterministic Vs. Probabilistic Models

Typically, computer-based systems use a mapping between observed symptoms of failure and the equipment where the mapping is built using deterministic techniques. The mapping typically takes the form of a look-up table, a symptom-problem matrix, trend analysis, and production rules. In stark contrast, alternatively probabilistic models are used to analyze a system. An example of a probabilistic model, referred to herein as an intelligent data extraction system is provided, infra.

Intelligent Data Extraction System

Referring now to FIG. 1, an algorithm based intelligent data extraction system 100 is illustrated. The intelligent data extraction system 100 uses a controller 110 to control a sensor 120. The sensor 120 is used to measure a parameter and/or is incorporated into a biomedical apparatus 130. Optionally, the controller 110 additionally controls the medical apparatus and/or is built into the biomedical apparatus 130. The sensor 120 provides readings to a data processor or a probabilistic digital signal processor 200, which provides feedback to the controller 110 and/or provides output 150. In one embodiment, the controller 110 comprises a microprocessor in a computer or computer system, an embedded device, and/or an embedded processor.

Herein, to enhance understanding and for clarity of presentation, non-limiting examples of an intelligent data extraction system operating on a hemodynamics biomedical devices are used to illustrate methods, systems, and apparatus described herein. Generally, the methods, systems, and apparatus described herein extend to any apparatus having a moveable part and/or to any medical device. Examples of the dynamic state-space model with a probabilistic digital signal processor used to estimate parameters of additional biomedical systems are provided after the details of the processing engine are presented.

Still referring to FIG. 1, in a pulse oximeter example the controller 110 controls a sensor 120 in the pulse oximeter apparatus 130. The sensor 120 provides readings, such as a spectral reading to the probabilistic digital signal processor 200, which is preferably a probability based data processor. The probabilistic digital signal processor 200 optionally operates on the input data or provides feedback to the controller 110, such as state of the patient, as part of a loop, iterative loop, time series analysis, and/or generates the output 150, such as a smoothed biomedical state parameter or a new biomedical state parameter. For clarity, the pulse oximeter apparatus is used repetitively herein as an example of the biomedical apparatus 130 upon which the intelligent data extraction system 100 operates. The probabilistic digital signal processor 200 is further described, infra.

Data Processor

Figure 2:
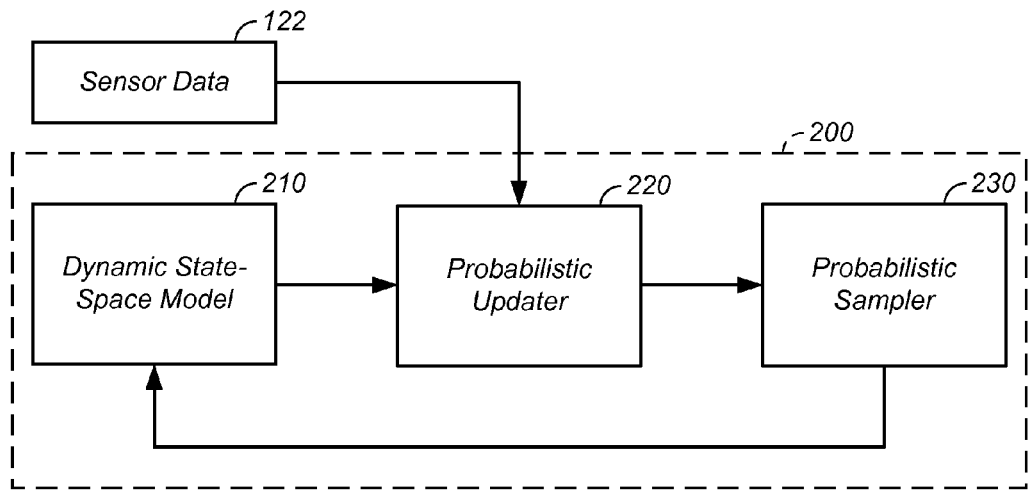
FIG. 2 provides a block diagram of a data processor.

Referring now to FIG. 2, the probabilistic digital signal processor 200 of the intelligent data extraction system 100 is further described. Generally, the data processor includes a dynamic state-space model 210 (DSSM) and a probabilistic updater 220 that iteratively or sequentially operates on sensor data 122 from the sensor 120. The probabilistic updater 220 outputs a probability distribution function to a parameter updater or a probabilistic sampler 230, which generates one or more parameters, such as an estimated diagnostic parameter, which is sent to the controller 110, is used as part of an iterative loop as input to the dynamic state-space model 210, and/or is a basis of the output 150. The dynamic state-space model 210 and probabilistic updater 220 are further described, infra.

Figure 3:
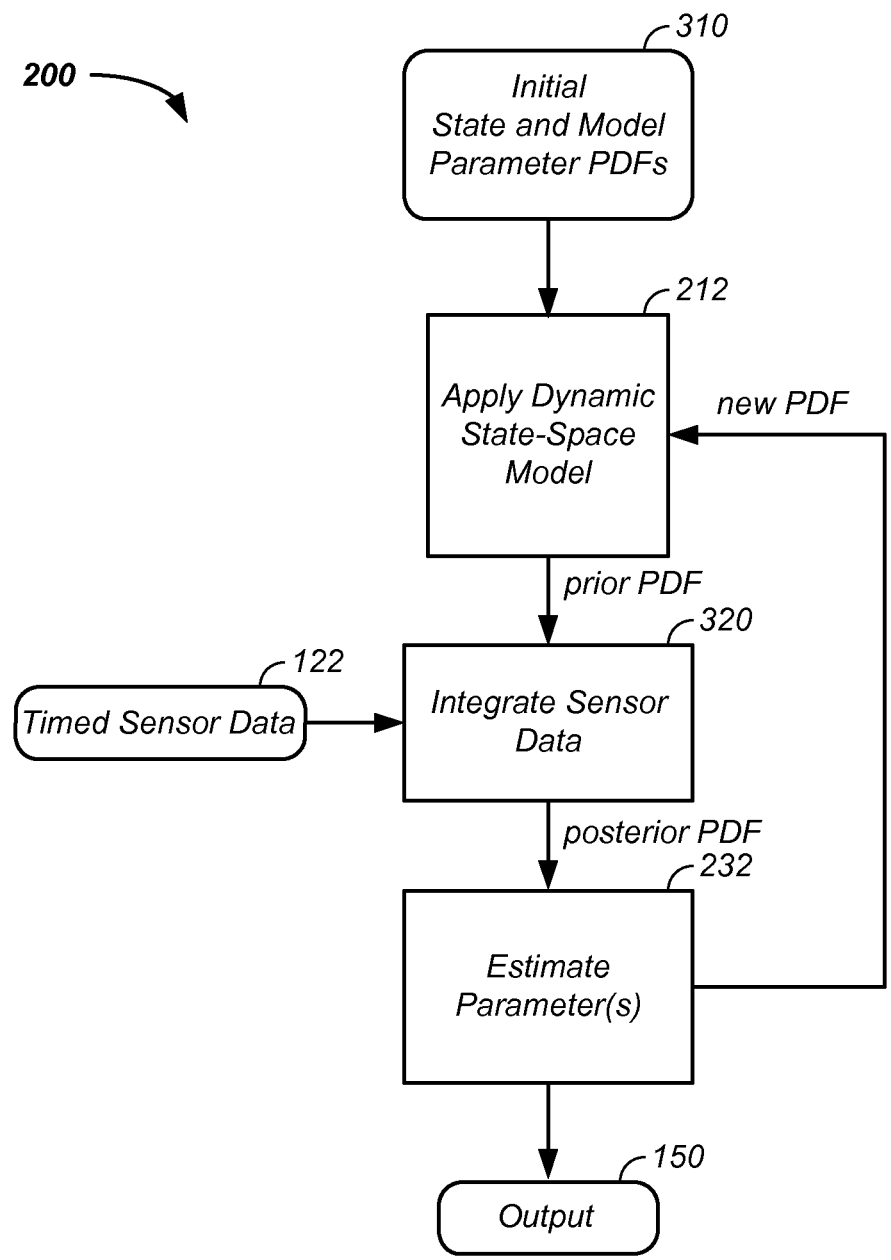
FIG. 3 is a flow diagram of a probabilistic digital signal processor.

Referring now to FIG. 3, the probabilistic digital signal processor 200 is further described. Generally, a probability function, a probability distribution function (PDF), an initial probability distribution function, or a set of initial probability distribution functions 310 are input to the dynamic state-space model 210. In a process 212, the dynamic state-space model 210 operates on the initial probability distribution functions 310 to generate a prior probability distribution function, hereinafter also referred to as a prior or as a prior PDF. For example, an initial state parameter 312 probability distribution function and an initial model parameter 314 probability distribution function are provided as initial inputs to the dynamic state-space model 210. The dynamic state-space model 210 operates on the initial state parameter 312 and/or initial model parameter 314 to generate the prior probability distribution function, which is input to the probabilistic updater 220. In a process 320, the probabilistic updater 220 integrates sensor data, such as timed sensor data 122, by operating on the sensor data and on the prior probability distribution function to generate a posterior probability distribution function, herein also referred to as a posterior or as a posterior PDF. In a process 232, the probabilistic sampler 230 estimates one or more parameters using the posterior probability distribution function. The probabilistic sampler 230 operates on the state and model parameter probability distribution functions from the state and model parameter updaters 224, 226, respectively or alternatively operates on the joint parameter probability distribution function and calculates an output. The output is optionally:

the state or joint parameter PDF, passed to the PDF resampler 520; and/or;

output values resulting from an operation on the inputs to the output 150 or output display or to the 110 controller.

In one example, expectation values such as a mean and a standard deviation of a state parameter are calculated from the state parameter PDF and output to the user, such as for diagnosis. In another example, expectation values, such as a mean value of state and model parameters, are calculated and then used in a model to output a more advanced diagnostic or prognostic parameter. In a third example, expectation values are calculated on a PDF that is the result of an operation on the state parameter PDF and/or model parameter PDF. Optionally, the output is to the same parameter as the state parameter PDF or model parameter PDF. Other data, such as user-input data, is optionally used in the output operation. The estimated parameters of the probabilistic sampler 230 are optionally used as a feedback to the dynamic state-space model 210 or are used to estimate a biomedical parameter. The feedback to the dynamic state-space model 210 is also referred to as a new probability distribution function or as a new PDF, which is/are updates of the initial state parameter 312 and/or are updates of the initial model parameter 314. Again, for clarity, an example of an estimated parameter 232 is a measurement of the heart/cardiovascular system, such as a heartbeat stroke volume.

Dual Estimator

Figure 4:
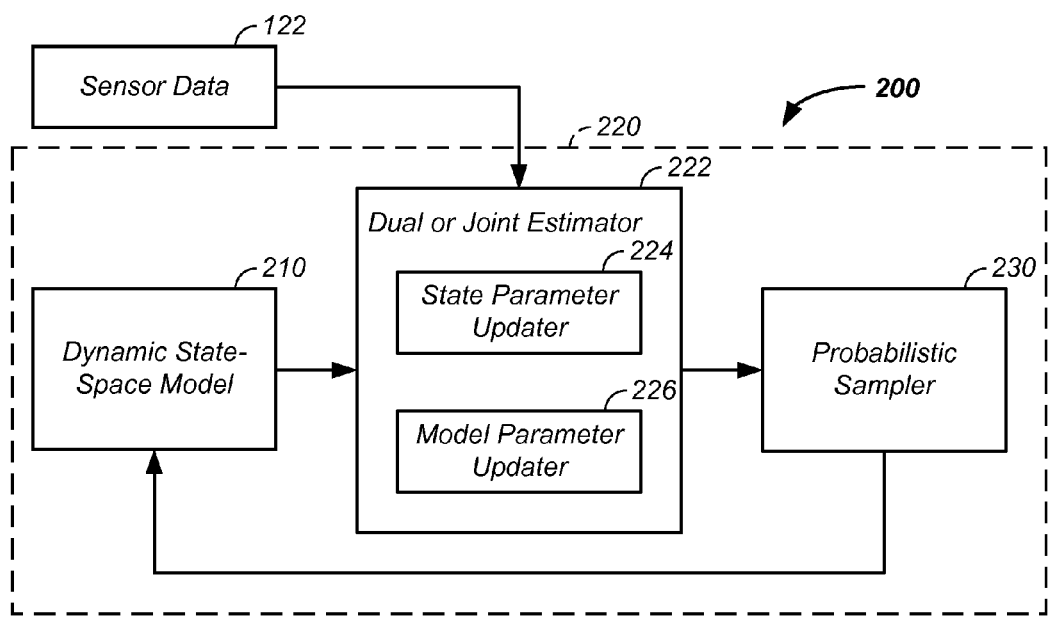
FIG. 4 illustrates a dual estimator.

In another embodiment, the probabilistic updater 220 of the probabilistic digital signal processor 200 uses a dual or joint estimator 222. Referring now to FIG. 4, the joint estimator 222 or dual estimation process uses both a state parameter updater 224 and a model parameter updater 226. Herein, for clarity, a dual estimator 222 is described. However, the techniques and steps described herein for the dual estimator are additionally applicable to a joint estimator as the state parameter and model parameter vector and/or matrix of the dual estimator are merely concatenated in a joint parameter vector and/or are joined in a matrix in a joint estimator.

State Parameter Updater

A first computational model used in the probabilistic updater 220 includes one or more state variables or state parameters, which correspond to the parameter being estimated by the state parameter updater 224. In the case of the hemodynamics monitoring apparatus, state parameters include time, intensity, reflectance, and/or a pressure. Some or all state parameters are optionally selected such that they represent the "true" value of noisy timed sensor data. In this case, calculation of such a posterior state parameter PDF constitutes a noise filtering process and expectation values of the PDF optionally represent filtered sensor values and associated confidence intervals.

Model Parameter Updater

A second computational model used in the probabilistic updater 220 includes one or more model parameters updated in the model parameter updater 226. For example, in the case of the hemodynamics monitoring apparatus, model parameters include: a time interval, a heart rate, a stroke volume, and/or a blood oxygenation percentage.

Hence, the dual estimator 222 optionally simultaneously or in a processing loop updates or calculates one or both of the state parameters and model parameters. The probabilistic sampler 230 is used to determine the estimated value for the biomedical parameter, which is optionally calculated from a state parameter, a model parameter, or a combination of one or more of the state parameter and/or the model parameter.

Figure 5:
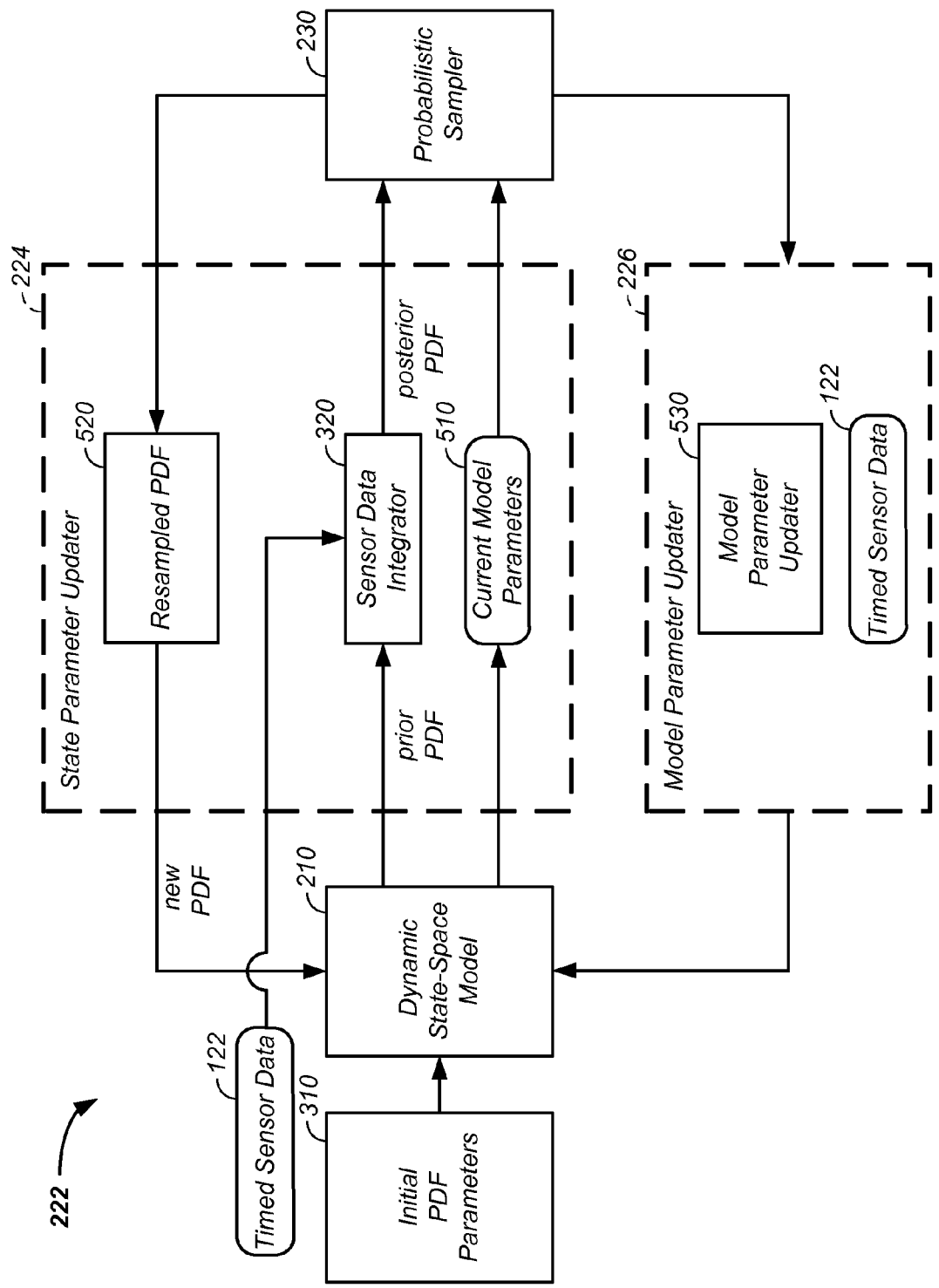
FIG. 5 expands the dual estimator.

Referring still to FIGS. 3 and 4 and now referring to FIG. 5, a first example of the dual estimator 222 is described and placed into context of the dynamic state-space model 210 and probabilistic sampler 230 of the probabilistic digital signal processor 200. The state parameter updater 224 element of the dual estimator 222 optionally:

uses a sensor data integrator 320 operating on the prior PDF being passed from the dynamic state-space model 210 and optionally operates on new timed sensor data 122, to produce the posterior PDF passed to the probabilistic sampler 230;

operates on current model parameters 510; and/or in a process 520, the state parameter updater 224 optionally re-samples a probability distribution function passed from the probabilistic sampler 230 to form the new probability distribution function passed to the dynamic state-space model 210.

In addition, in a process 530 the model parameter updater 226 optionally integrates new timed sensor data 122 with output from the probabilistic sampler 230 to form new input to the dynamic state-space model 210.

Figure 6:
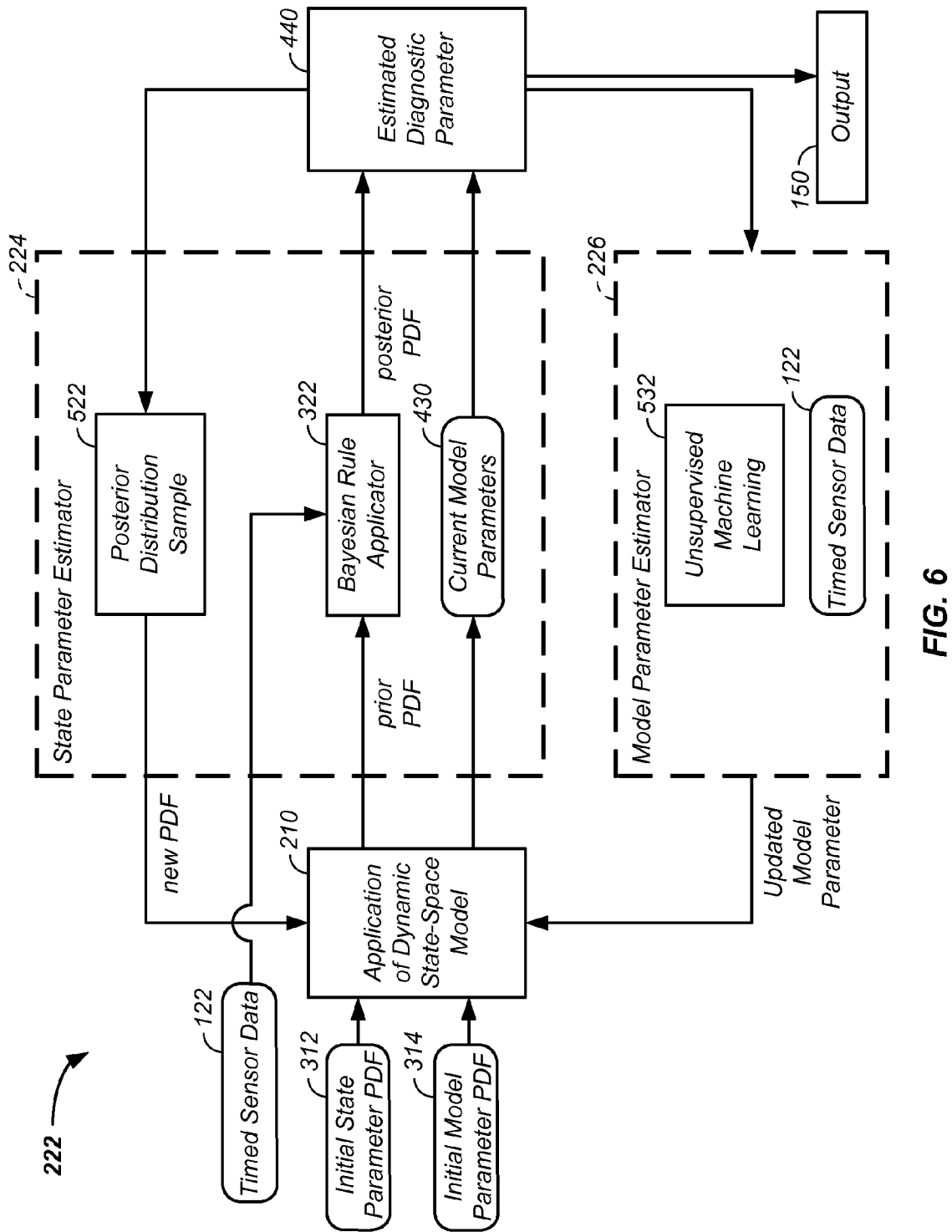
FIG. 6 illustrates state and model parameter estimators.

Referring now to FIG. 6, a second example of a dual estimator 222 is described. In this example:

initial state parameter probability distribution functions 312 are passed to the dynamic state-space model 210; and/or initial model parameter probability distribution functions 314 are passed to the dynamic state-space model 210.

Further, in this example:

a Bayesian rule applicator 322 is used as an algorithm in the sensor data integrator 320;

a posterior distribution sample algorithm 522 is used as the algorithm in the resampling of the PDF process 520; and a supervised or unsupervised machine learning algorithm 532 is used as the algorithm in the model parameter updater 530.

Optionally, a data driven model is used, such as a model using a neural network.

Filtering

In various embodiments, algorithms, data handling steps, and/or numerical recipes are used in a number of the steps and/or processes herein. The inventor has determined that several algorithms are particularly useful: sigma point Kalman filtering, sequential Monte Carlo filtering, and/or use of a sampler. In a first example, either the sigma point Kalman filtering or sequential Monte Carlo algorithms are used in generating the probability distribution function. In a second example, either the sigma point Kalman filtering or sequential Monte Carlo algorithms are used in the unsupervised machine learning 532 step in the model parameter updater 530 to form an updated model parameter. The sigma point Kalman filtering, sequential Monte Carlo algorithms, and use of a sampler are further described, infra.

Sigma Point Kalman Filter

Filtering techniques based on Kalman and extended Kalman techniques offer advantages over conventional methods and work well for filtering linear systems or systems with small nonlinearities and Gaussian noise. These Kalman filters, however, are not optimum for filtering highly nonlinear systems and/or non-Gaussian/non-stationary noise. In stark contrast, sigma point Kalman filters are well suited to data having nonlinearities and non-Gaussian noise.

Herein, a sigma point Kalman filter (SPKF) refers to a filter using a set of weighted sigma-points that are deterministically calculated, such as by using the mean and square-root decomposition, or an equivalent, of the covariance matrix of a probability distribution function to about capture or completely capture at least the first and second order moments. The sigma-points are subsequently propagated in time through the dynamic state-space model 210 to generate a prior sigma-point set. Then, prior statistics are calculated using tractable functions of the propagated sigma-points, weights, and new measurements.

Sigma point Kalman filter advantages and disadvantages are described herein. A sigma point Kalman filter interprets a noisy measurement in the context of a mathematical model describing the system and measurement dynamics. This gives the sigma point Kalman filter inherent superior performance to all "model-less" methods, such as Wiener filtering, wavelet de-noising, principal component analysis, independent component analysis, nonlinear projective filtering, clustering methods, adaptive noise cancelling, and many others.

A sigma point Kalman filter is superior to the basic Kalman filter, extended Kalman filter, and related variants of the Kalman filters. The extended Kalman filter propagates the random variable using a single measure, usually the mean, and a first order Taylor expansion of the nonlinear dynamic state-space model 210. Conversely, a sigma point Kalman filter decomposes the random variable into distribution moments and propagates those using the unmodified nonlinear dynamic state-space model 210. As a result, the sigma point Kalman filter yields higher accuracy with equal algorithm complexity, while also being easier to implement in practice.

In the sigma-point formalism the probability distribution function is represented by a set of values called sigma points, those values represent the mean and other moments of the distribution which, when input into a given function, recovers the probability distribution function.

Sequential Monte Carlo

Sequential Monte Carlo (SMC) methods approximate the prior probability distribution function through use of a set of weighted sample values without making assumptions about its form. The samples are then propagated in time through the unmodified dynamic state-space model 210. The resulting samples are used to update the posterior via Bayes rule and the latest noisy measurement or timed sensor data 122.

In the sequential Monte Carlo formalism the PDF is actually discretized into a collection of probability "particles" each representing a segment of the probability density in the probability distribution function.

SPKF and SMC

In general, sequential Monte Carlo methods have analysis advantages compared to the sigma point Kalman filters, but are more computationally expensive. However, the SPKF uses a sigma-point set, which is an exact representation only for Gaussian probability distribution functions (PDFs). As a result, SPKFs lose accuracy when PDFs depart heavily from the Gaussian form, such as with bimodal, heavily-tailed, or nonstationary distributions. Hence, both the SMC and SPKF filters have advantages. However, either a SMC analysis or SPKF is used to propagate the prior using the unmodified DSSM. Herein, generally when a SMC filter is used a SPKF filter is optionally used and vise-versa.

A SPKF or a SMC algorithm is used to generate a reference signal in the form of a first probability distribution from the model's current (time=t) physiological state. The reference signal probability distribution and a probability distribution generated from a measured signal from a sensor at a subsequent time (time=t+n) are convoluted using Bayesian statistics to estimate the true value of the measured physiological parameter at time=t+n. The probability distribution function is optionally discrete or continuous. The probability distribution function is optionally used to identify the probability of each value of an unidentified random variable, such as in a discrete function, or the probability of the value falling within a particular interval, such as in a continuous function.

Sampler

Probability distribution functions (PDFs) are optionally continuous or discrete. In the continuous case the probability distribution function is represented by a function. In the discrete case, the variable space is binned into a series of discrete values. In both the continuous and discrete cases, probability distribution functions are generated by first decomposing the PDF into a set of samplers that are characteristic of the probability distribution function and then the samplers are propagated via computations through the DSSM (prior generation) and sensor data integrator (posterior generation). Herein, a sampler is a combination of a value and label. The value is associated with the x-axis of the probability distribution function, which denotes state, model, or joint parameters. The label is associated with the y-axis of the probability distribution function, which denotes the probability. Examples of labels are: weight, frequency, or any arbitrary moment of a given distribution, such as a first Gaussian moment. A powerful example of characteristic sampler use is decomposing the PDF into a series of state values with attached first Gaussian moment labels. This sum of several Gaussian distributions with different values and moments usually gives accurate approximations of the true probability distribution function.

Probabilistic Digital Signal Processor

As described, supra, in various embodiments, the probabilistic digital signal processor 200 comprises one or more of a dynamic state-space model 210, a dual or joint estimator 222, and/or a probabilistic sampler 230, which processes input data, such as sensor data 122 and generates an output 150. Preferably, the probabilistic digital signal processor 200 (1) iteratively processes the data and/or (2) uses a physical model in processing the input data.

The probabilistic digital signal processor 200 optionally:
 filters input data;
 operates using data from a medical meter, where the medical meter yields a first physical parameter from raw data, to generate a second physical parameter not output by the medical meter;
 operates on discrete/non-probabilistic input data from a medical device to generate a probabilistic output function;
 iteratively circulates a probability distribution function through at least two of the dynamic state-space model, the dual or joint updater, and/or the probabilistic sampler;
 fuses or combines output from multiple medical devices; and/or
 prognosticates probability of future events.

A hemodynamics example of a probabilistic digital signal processor 200 operating on data from a pulse oximeter is used to describe these processes, infra.

Dynamic State-Space Model

The dynamic state-space model 210 is further described herein.

Figure 7:
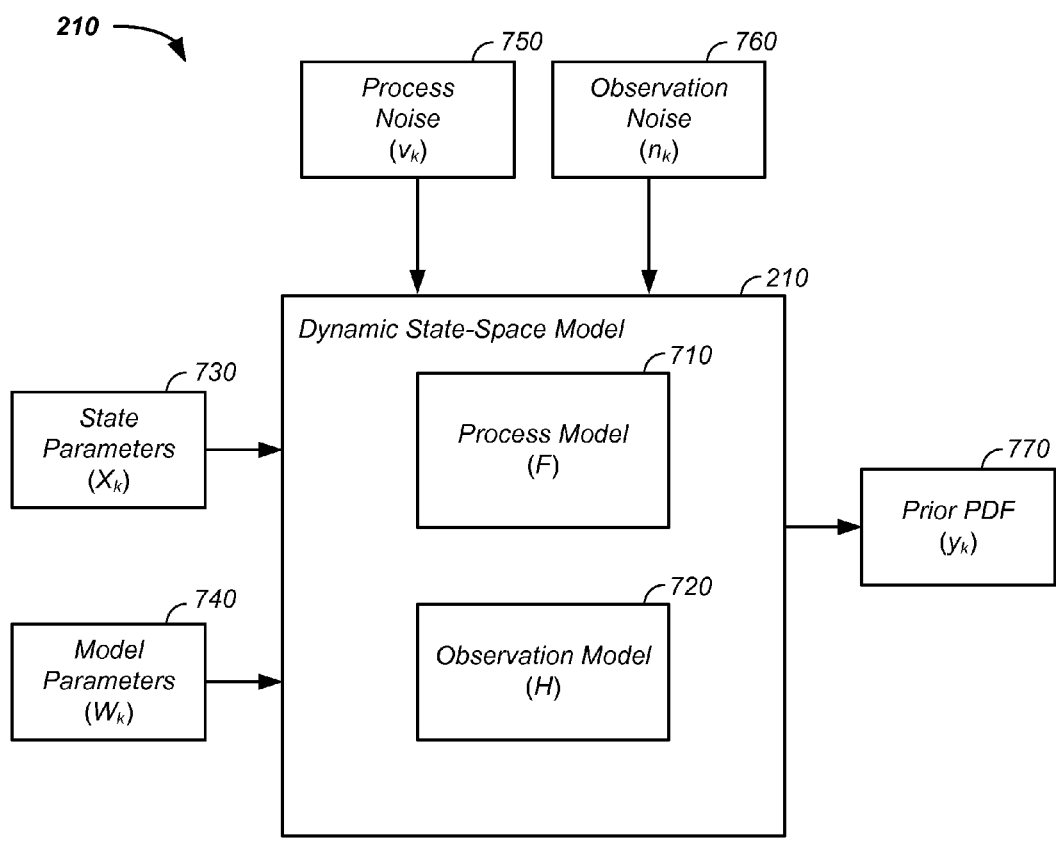
FIG. 7 provides inputs and internal operation of a dynamic state-space model.

Referring now to FIG. 7, schematics of an exemplary dynamic state-space model 210 (DSSM) used in the processing of data is provided. The dynamic state-space model 210 typically and optionally includes a process model 710 and/or an observation model 720. The process model 710, F, which mathematically represents mechanical processes involved in generating one or more biomedical parameters, is measured by a sensor, such as a sensor sensing a mechanical component and describes the state of the biomedical apparatus, output of the biomedical apparatus, and/or state of the patient over time in terms of state parameters. This mathematical model optimally includes mathematical representations accounting for process noise 750, such as mechanically caused artifacts that may cause the sensor to produce a digital output that does not produce an accurate measurement for the biomedical parameter being sensed. The dynamic state-space model 210 also comprises an observational model 720, H, which mathematically represents processes involved in collecting sensor data measured by the mechanical sensor. This mathematical model optimally includes mathematical representations accounting for observation noise produced by the sensor apparatus that may cause the sensor to produce a digital output that does not produce an accurate measurement for a biomedical parameter being sensed. Noise terms in the mathematical models are not required to be additive.

While the process and observation mathematical models 710, 720 are optionally conceptualized as separate models, they are preferably integrated into a single mathematical model that describes processes that produce a biomedical parameter and processes involved in sensing the biomedical parameter. The integrated process and observation model, in turn, is integrated with a processing engine within an executable program stored in a data processor, which is configured to receive digital data from one or more sensors and to output data to a display and/or to another output format.

Still referring to FIG. 7, inputs into the dynamic state-space model 210 include one or more of:
  state parameters 730, such as the initial state parameter probability distribution function 312 or the new PDF;
  model parameters 740, such as the initial noise parameter probability distribution function 314 or an updated model parameter from the unsupervised machine learning module 532;
  process noise 750; and/or
  observation noise 760.

Hemodynamics Dynamic State-Space Model

Figure 8:
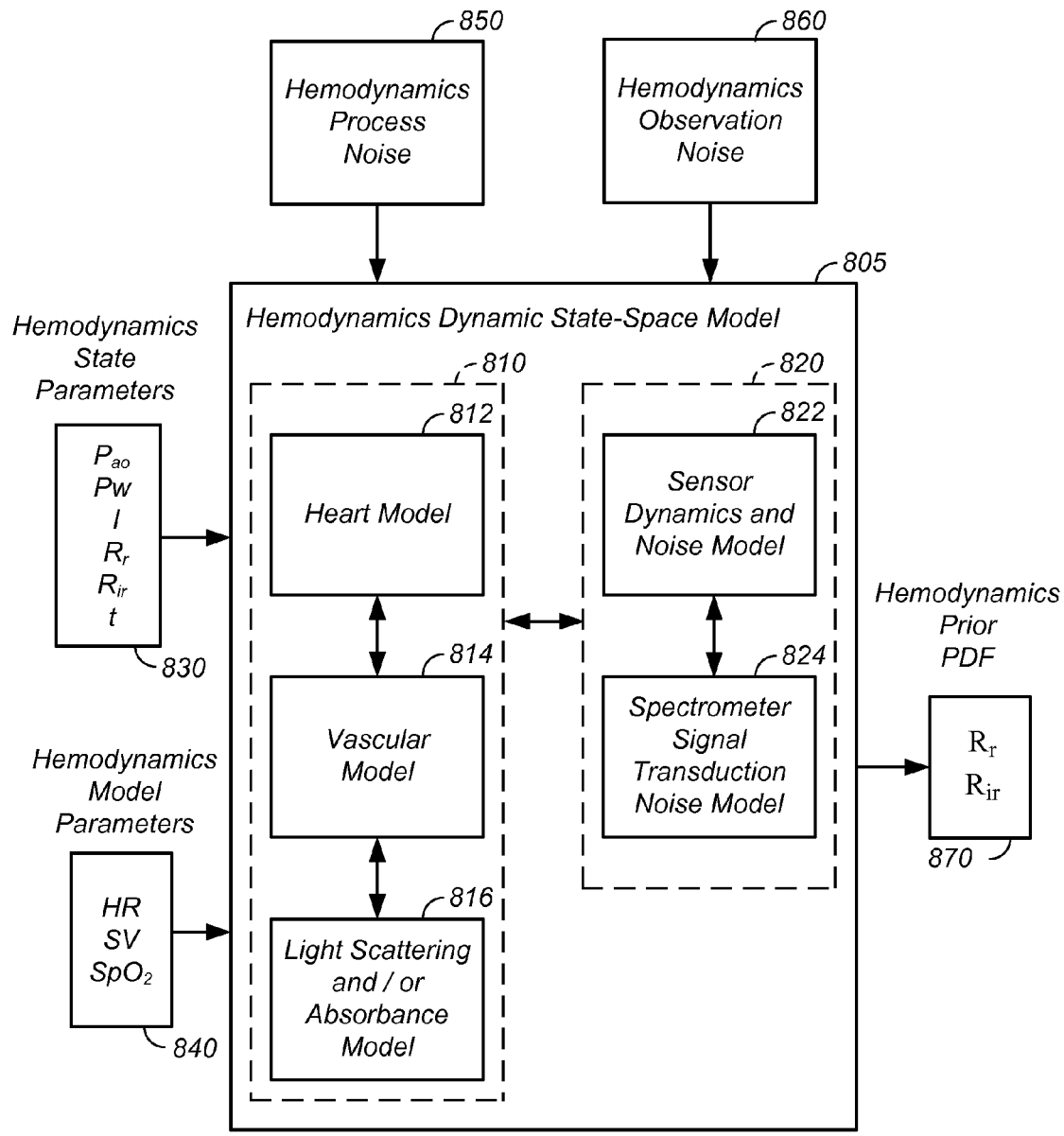
FIG. 8 is a flow chart showing the components of a hemodynamics dynamic state-space model.
Figure 9A:
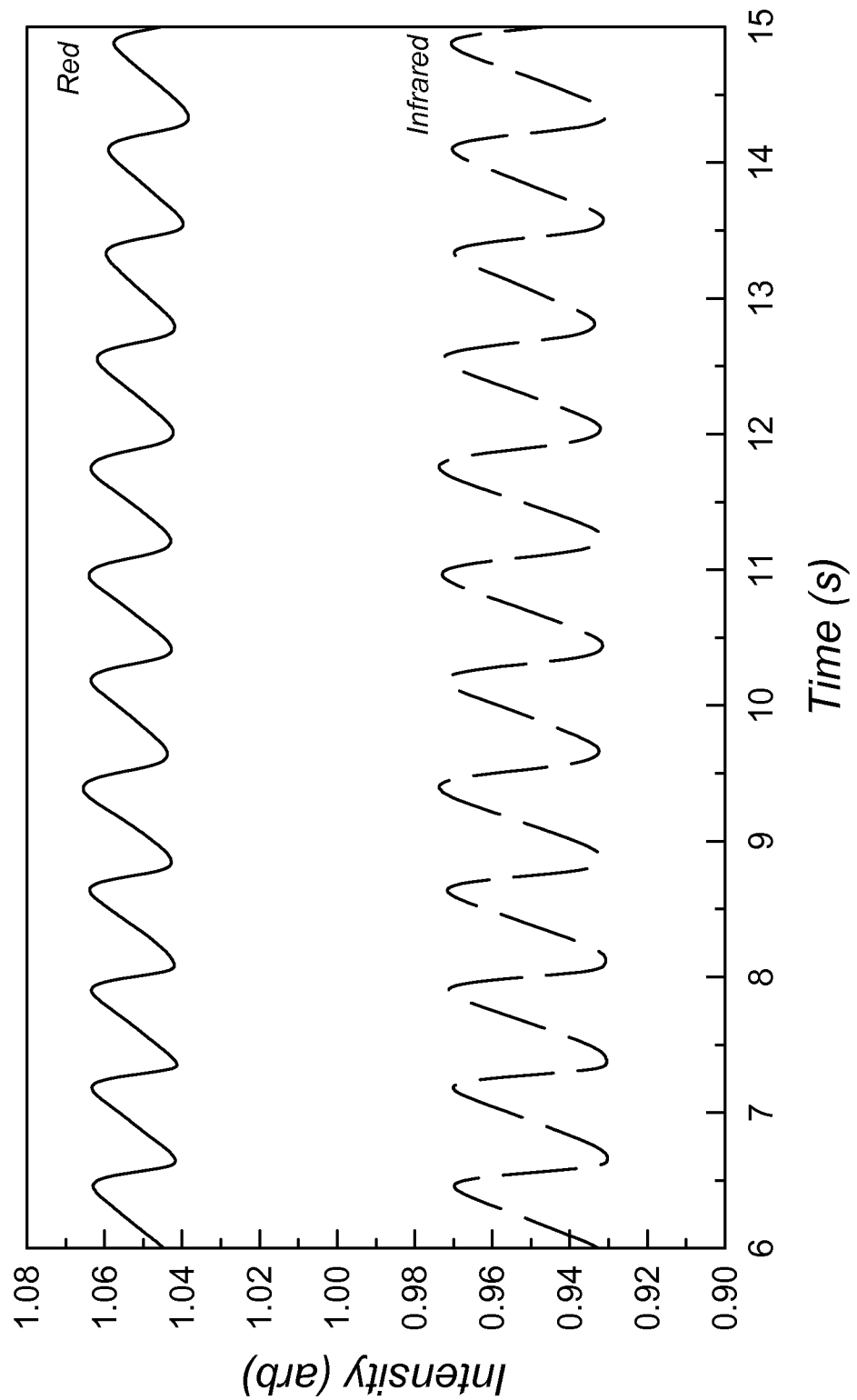
FIG. 9 is a chart showing input sensor data, FIG. 9A; processed output data of heart rate, FIG. 9B; stroke volume, FIG. 9C; cardiac output, FIG. 9D; oxygen, FIG. 9E; and pressure, FIG. 9F, from a data processor configured to process pulse oximetry data.
Figure 9B:
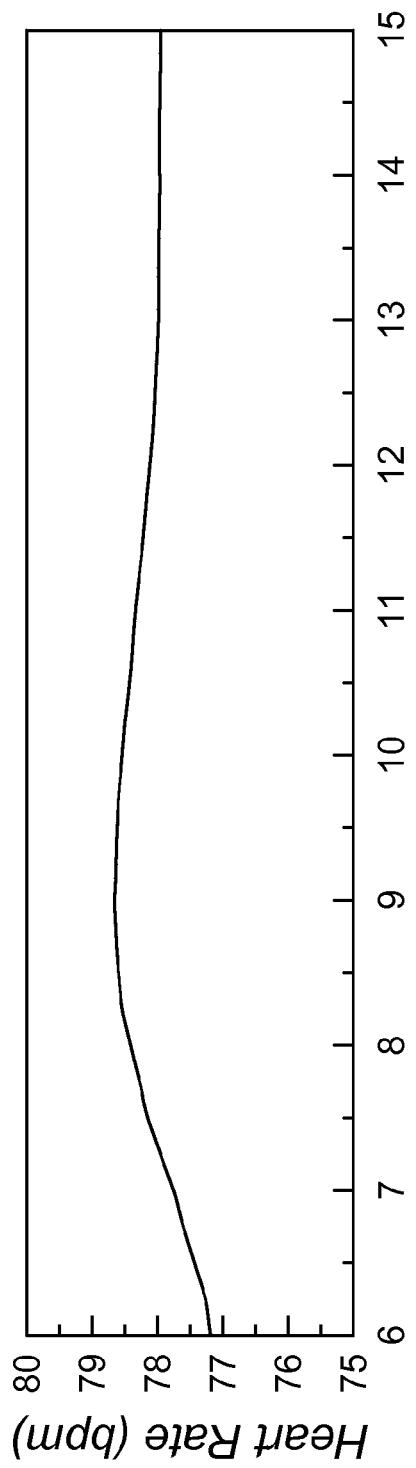
Figure 9C:
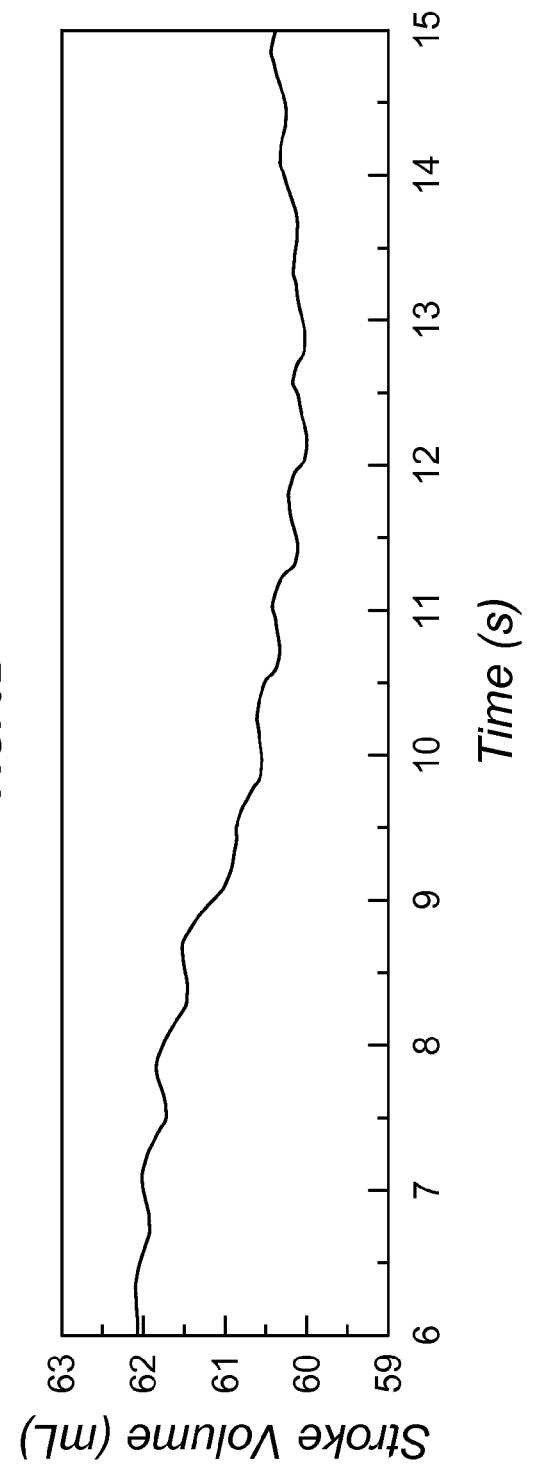
Figure 9F:
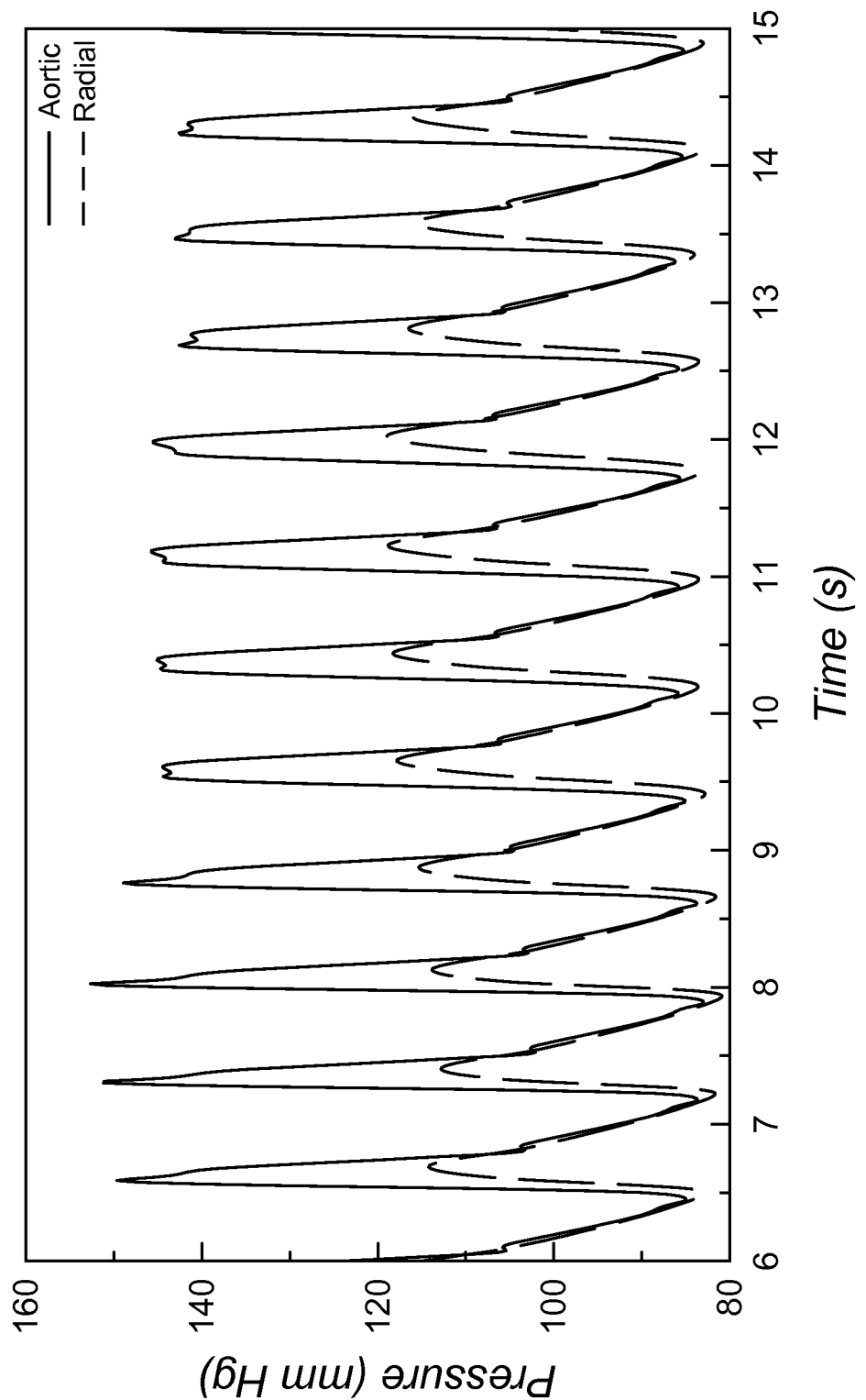
Figure 10A:
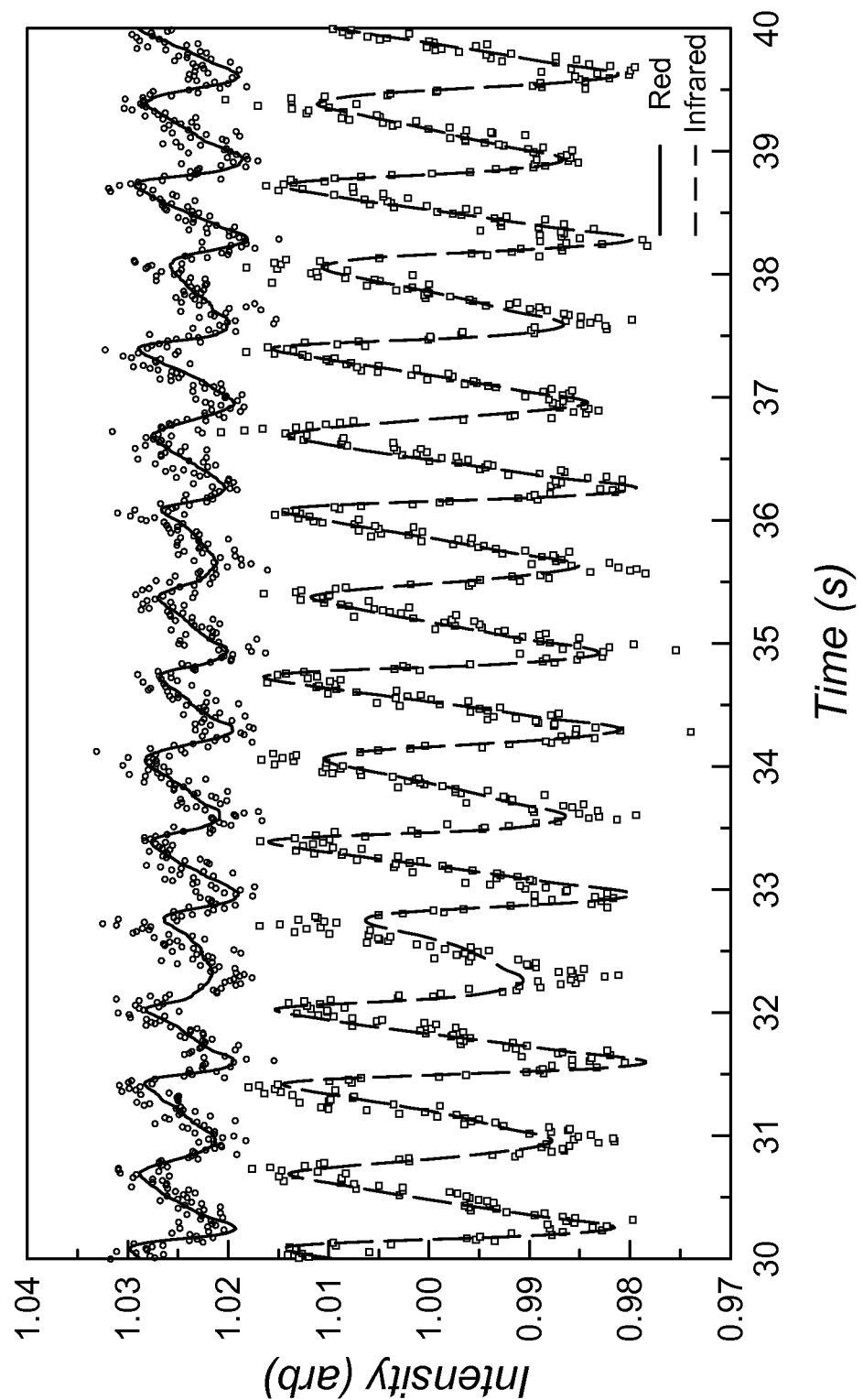
FIG. 10 is a chart showing input sensor data, FIG. 10A, and processed output data, FIGS. 10A-10E, from a data processor configured to process pulse oximetry data under a low blood perfusion condition.
Figure 10B:
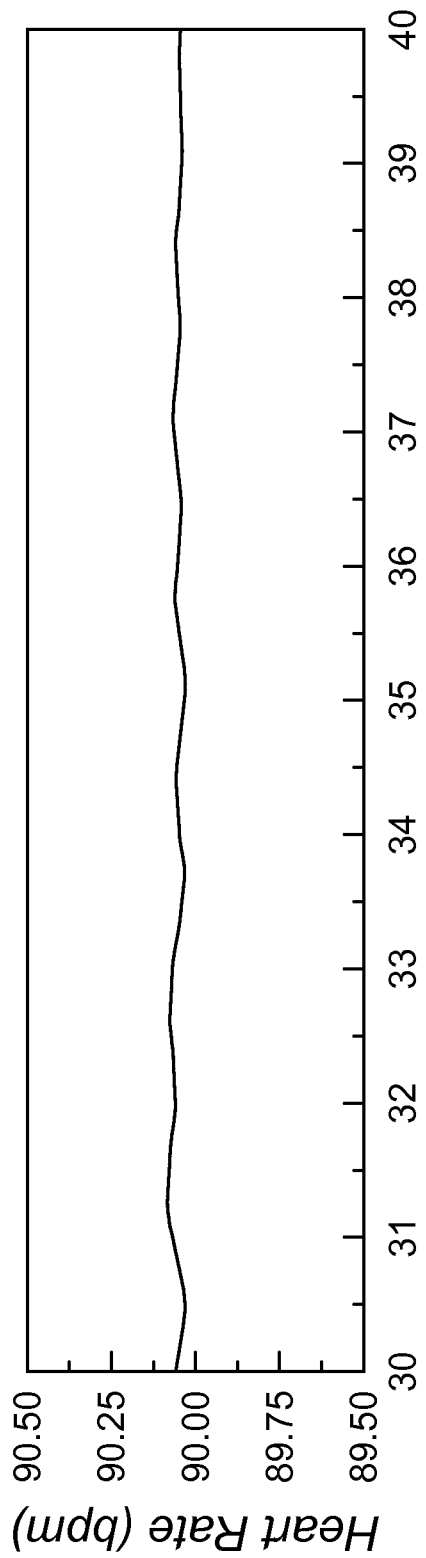
Figure 10C:
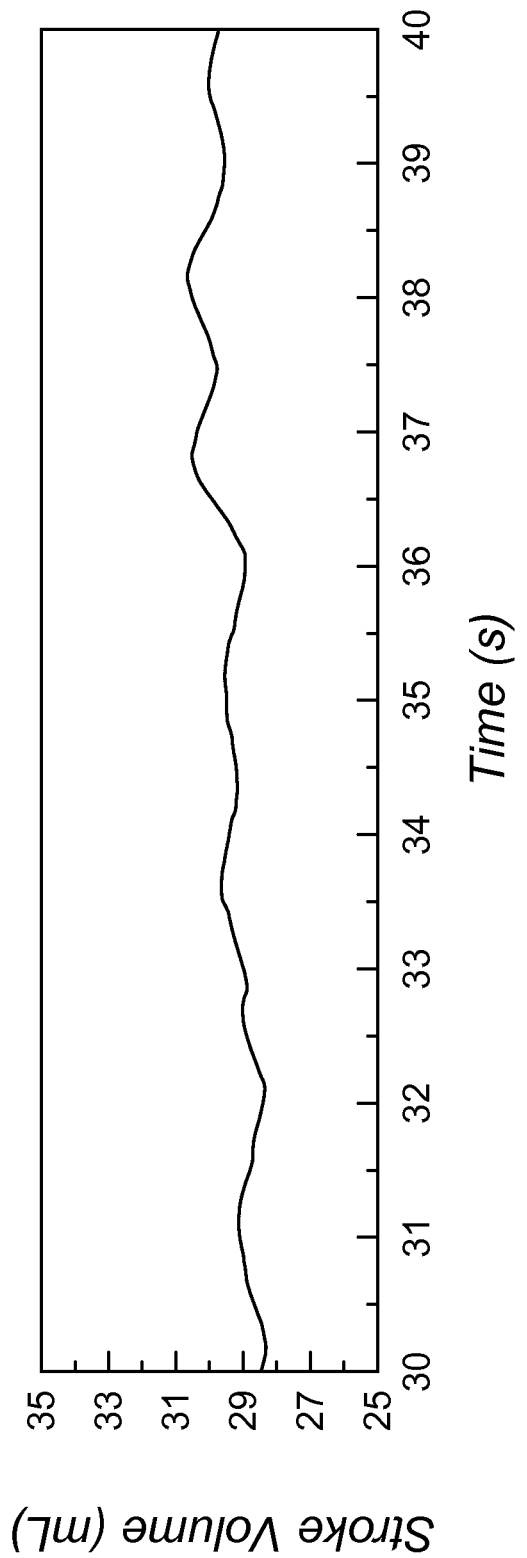
Figure 10D:
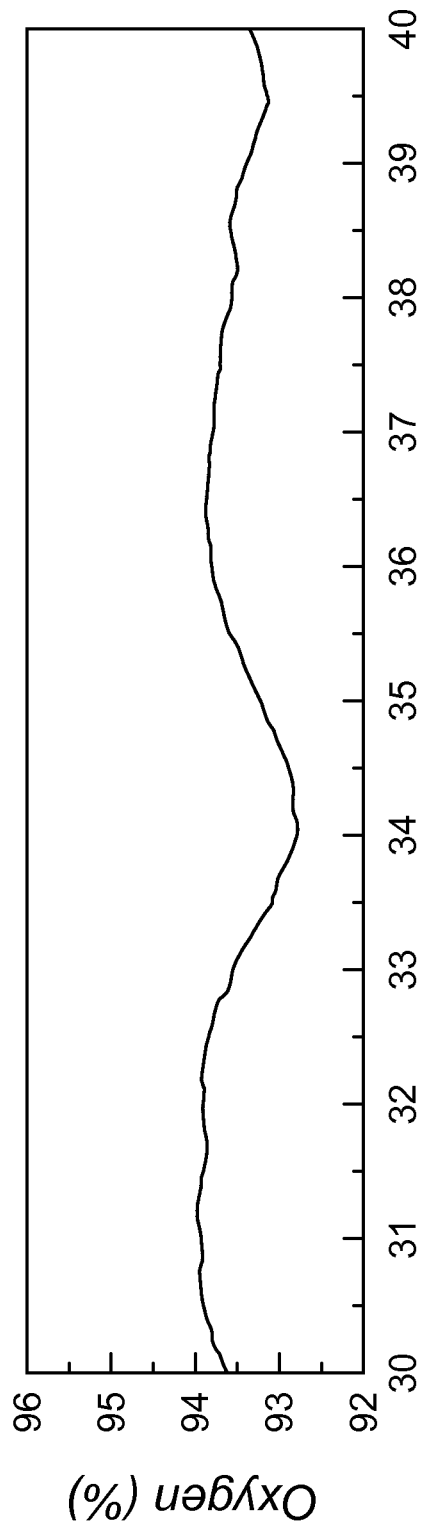
Figure 10E:
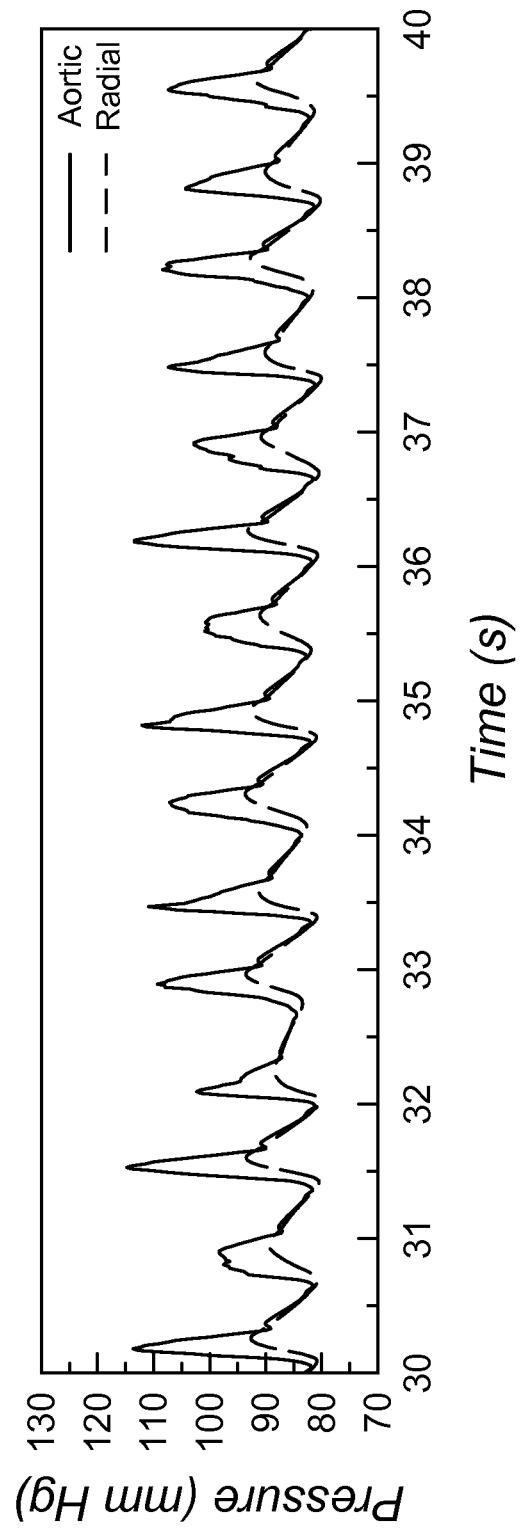

A first non-limiting specific example is used to facilitate understanding of the dynamic state-space model 210. Referring now to FIG. 8, a hemodynamics dynamic state-space model 805 flow diagram is presented. Generally, the hemodynamics dynamic state-space model 805 is an example of a dynamic state-space model 210. The hemodynamics dynamic state-space model 805 combines sensor data 122, such as a spectral readings of skin, with a physical parameter based probabilistic model. The hemodynamics dynamic state-space model 805 operates in conjunction with the probabilistic updater 220 to form an estimate of heart/cardiovascular state parameters.

To facilitate description of the probabilistic digital signal processor, a non-limiting example of a hemodynamics process model is provided. In this example, the probabilistic digital signal processor is provided:
  raw sensor data, such as current, voltage, and/or resistance; and/or
  a first physical parameter output from a medical device.

In this example, the medical device is a pulse oximeter collecting raw data and the first physical parameter from the pulse oximeter provided as input to the probabilistic digital signal processor is one or more of:
  a heart rate; and/or
  a blood oxygen saturation.

The probabilistic digital signal processor uses a physical model, such as a probabilistic model, to operate on the first physical parameter and/or the raw data to generate a second physical parameter, where the second physical parameter is optionally not the first physical parameter. For example, the output of the probabilistic digital signal processor using a physical hemodynamic model, when provided with the pulse oximeter data, is one or more of:
  a heart stroke volume;
  a cardiac output flow rate;
  an aortic blood pressure; and/or
  a radial blood pressure.

Optionally, the output from the probabilistic model is an updated, error filtered, and/or smoothed version of the original input data, such as a smoothed blood oxygen saturation percentage as a function of time.

Still referring to FIG. 8, to facilitate description of the hemodynamics dynamic state-space model 805, a non-limiting example is provided. In this example, the hemodynamics dynamic state-space model 805 is further described. The hemodynamics dynamic state-space model 805 preferably includes a hemodynamics process model 810 corresponding to the dynamic state-space model 210 process model 710. Further, the hemodynamics dynamic state-space model 805 preferably includes a hemodynamics observation model 820 corresponding to the dynamic state-space model 210 observation model 720. The hemodynamics process model 810 and hemodynamics observation model 820 are further described, infra.

Still referring to FIG. 8, the hemodynamics process model 810 optionally includes one or more of a heart model 812, a vascular model 814, and/or a light scattering or light absorbance model 816. The heart model 812 is a physics based probabilistic model of the heart and movement of blood in and/or from the heart. The vascular model 814 is a physics based probabilistic model of movement of blood in arteries, veins, and/or capillaries. The various models optionally share information. For example, blood flow or stroke volume exiting the heart in the heart model 812 is optionally an input to the arterial blood in the vascular model 814. The light scattering and/or absorbance model 816 relates spectral information, such as from a pulse oximeter, to additional hemodynamics dynamic state-space model parameters, such as heart rate (HR), stroke volume (SV), and/or whole-blood oxygen saturation ($SpO_2$) or oxyhemoglobin percentage.

Still referring to FIG. 8, the hemodynamics observation model 820 optionally includes one or more of a sensor dynamics and noise model 822 and/or a spectrometer signal transduction noise model 824. Each of the sensor dynamics and noise model 822 and the spectrometer signal transduction noise model 824 are physics based probabilistic models related to noises associated with the instrumentation used to collect data, environmental influences on the collected data, and/or noise due to the human interaction with the instrumentation, such as movement of the sensor. As with the hemodynamics process model 810, the sub-models of the hemodynamics observation model 820 optionally share information. For instance, movement of the sensor noise is added to environmental noise. Optionally and preferably, the hemodynamics observation model 820 shares information with and/or provides information to the hemodynamics process model 810.

The hemodynamics dynamic state-space model 805 receives inputs, such as one or more of:
- hemodynamics state parameters 830;
- hemodynamics model parameters 840;
- hemodynamics process noise 850; and
- hemodynamics observation noise 860.

Examples of hemodynamics state parameters 830, corresponding to state parameters 730, include: radial pressure ($P_w$), aortic pressure ($P_{ao}$), time (t), a spectral intensity (I) or a related absorbance value, a reflectance or reflectance ratio, such as a red reflectance ($R_r$) or an infrared reflectance ($R_{ir}$), and/or a spectral intensity ratio ($I_R$). Examples of hemodynamics model parameters 840, corresponding to the more generic model parameters 740, include: heart rate (HR), stroke volume (SV), and/or whole-blood oxygen saturation ($SpO_2$). In this example, the output of the hemodynamics dynamic state-space model 805 is a prior probability distribution function with parameters of one or more of the input hemodynamics state parameters 830 after operation on by the heart dynamics model 812, a static number, and/or a parameter not directly measured or output by the sensor data. For instance, an input data stream is optionally a pulse oximeter yielding spectral intensities, ratios of intensities, and a percent oxygen saturation. However, the output of the hemodynamics dynamic state-space model is optionally a second physiological value, such as a stroke volume of the heart, which is not measured by the input biomedical device.

The hemodynamics dynamic state-space model 805 optionally receives inputs from one or more additional models, such as an irregular sampling model, which relates information collected at irregular or non-periodic intervals to the hemodynamics dynamic state-space model 805.

Generally, the hemodynamics dynamic state-space model 805 is an example of a dynamic state-space model 210, which operates in conjunction with the probabilistic updater 220 to form an estimate of a heart state parameter and/or a cardiovascular state parameter.

Generally, the output of the probabilistic signal processor 200 optionally includes a measure of uncertainty, such as a confidence interval, a standard deviation, and/or a standard error. Optionally, the output of the probabilistic signal processor 200 includes:
- a filtered or smoothed version of the parameter measured by the medical meter; and/or
- a probability function associated with a parameter not directly measured by the medical meter.

EXAMPLE I

An example of a pulse oximeter with probabilistic data processing is provided as an example of the hemodynamics dynamic state-space model 805. The model is suitable for processing data from a pulse oximeter model. In this example, particular equations are used to further describe the hemodynamics dynamic state-space model 805, but the equations are illustrative and non-limiting in nature.

Heart Model

An example of the heart model 812 is used to further described an example of the hemodynamics dynamic state-space model 805. In this example, cardiac output is represented by equation 1, $$Q_{CO}(t) = \overline{Q}_{CO} \sum_{1}^{\delta} a_k \exp\left[\frac{-(t-b_k)^2}{c_k^2}\right] \quad (1)$$

where cardiac output $Q_{co}(t)$, is expressed as a function of heart rate (HR) and stroke volume (SV) and where $Q_{co}$=(HR× SV)/60. The values $a_k$, $b_k$, and $c_k$ are adjusted to fit data on human cardiac output.

Vascular Model

An example of the vascular model 814 of the hemodynamics state-space model 805 is provided. The cardiac output function pumps blood into a Windkessel 3-element model of the vascular system including two state variables: aortic pressure, $P_{ao}$, and radial (Windkessel) pressure, $P_w$, according to equations 2 and 3, $$P_{w,k+1} = \frac{1}{C_w R_p}((R_P + Z_0)Q_{CO} - P_{CO,k})\delta t + P_{w,k} \quad (2)$$

$$P_{ao,k+1} = P_{w,k+1} + Z_0 Q_{CO} \quad (3)$$

where $R_p$ and $Z_o$ are the peripheral resistance and characteristic aortic impedance, respectively. The sum of these two terms is the total peripheral resistance due to viscous (Poiseuille-like) dissipation according to equation 4, $$Z_0 = \sqrt{\rho/AC_l} \quad (4)$$

where $\rho$ is blood density and $C_l$ is the compliance per unit length of artery. The elastic component due to vessel compliance is a nonlinear function including thoracic aortic cross-sectional area, A: according to equation 5, $$A(P_{CO}) = A_{max}\left[\frac{1}{2} + \frac{1}{\pi}\arctan\left(\frac{P_{CO} - P_0}{P_1}\right)\right] \quad (5)$$

where $A_{max}$, $P_O$, and $P_1$ are fitting constants correlated with age and gender according to equations 6-8.

$$A_{max} = (5.62 - 1.5(\text{gender})) \cdot cm^2 \quad (6)$$

$$P_0 = (76 - 4(\text{gender}) - 0.89(\text{age})) \cdot mmHg \quad (7)$$

$$P_1(57 - 0.44(\text{age})) \cdot mmHg \quad (8)$$

The time-varying Windkessel compliance, $C_w$, and the aortic compliance per unit length, $C_l$, are related in equation 9, $$C_w = lC_l = l\frac{dA}{dP_\infty} = l\frac{A_{max}/(\pi P_1)}{1 + \left(\frac{P_\infty - P_0}{P_1}\right)} \quad (9)$$

where l is the aortic effective length. The peripheral resistance is defined as the ratio of average pressure to average flow. A set-point pressure, $P_{set}$, and the instantaneous flow related to the peripheral resistance, $R_p$, according to equation 10, $$R_P = \frac{P_{set}}{(HR \cdot SV)/60} \quad (10)$$

are used to provide compensation to autonomic nervous system responses. The value for $P_{set}$ is optionally adjusted manually to obtain 120 over 75 mmHg for a healthy individual at rest.

Light Scattering and Absorbance Model

The light scattering and absorbance model 816 of the hemodynamics dynamic state-space model 805 is further described. The compliance of blood vessels changes the interactions between light and tissues with pulse. This is accounted for using a homogenous photon diffusion theory for a reflectance or transmittance pulse oximeter configuration according to equation 11, $$R = \frac{I_{ac}}{I_{dc}} = \frac{\Delta I}{I} = \frac{3}{2}\sum_{s}^{1} K(\alpha, d, r)\sum_{a}^{art} \Delta V_0 \quad (11)$$

for each wavelength. In this example, the red and infrared bands are centered at about 660±100 nm and at about 880±100 nm. In equation 11, 1 (no subscript) denotes the detected intensity, R, is the reflected light, and the alternating current intensity, $I_{ac}$, is the pulsating signal, ac intensity, or signal; and the background intensity, $I_{dc}$, is the direct current intensity or dc intensity; $\alpha$, is the attenuation coefficient; d, is the illumination length scale or depth of photon penetration into the skin; and r is the distance between the source and detector.

Referring again to the vascular model 814, $V_a$ is the arterial blood volume, which changes as the cross-sectional area of illuminated blood vessels, $\Delta A_w$, according to equation 12, $$\Delta V_a \approx r \cdot \Delta A_w \quad (12)$$

where r is the source-detector distance.

Referring again to the light scattering and absorbance model 816, the tissue scattering coefficient, $\Sigma_s'$, is assumed constant but the arterial absorption art coefficient, $\Sigma_a^{art}$, which represents the extinction coefficients, depends on blood oxygen saturation, $SpO_2$, according to equation 13, $$\sum_{a}^{art} = \frac{H}{v_i}[SpO_2 \cdot \sigma_0^{100\%} + (1-SpO_2) \cdot \sigma_0^{0\%}] \quad (13)$$

which is the Beer-Lambert absorption coefficient, with hematocrit, H, and red blood cell volume, $v_i$. The optical absorption cross-sections, proportional to the absorption coefficients, for red blood cells containing totally oxygenated ($HbO_2$) and totally deoxygenated (Hb) hemoglobin are $\sigma_a^{100\%}$ and $\sigma_a^{0\%}$, respectively.

The function $K(\alpha, d, r)$, along with the scattering coefficient, the wavelength, sensor geometry, and oxygen saturation dependencies, alters the effective optical pathlengths, according to equation 14.

$$K(\alpha, d, r) \approx \frac{-r^2}{1+\alpha r} \quad (14)$$

The attenuation coefficient $\alpha$ is provided by equation 15, $$\alpha = \sqrt{3\Sigma_a(\Sigma_s + \Sigma_a)} \quad (15)$$

where $\Sigma_a$ and $\Sigma_s$ are whole-tissue absorption and scattering coefficients, respectively, which are calculated from Mie Theory.

Red, $\overline{K_r}$, and infrared, $\overline{K_{ir}}$, K values as a function of $SpO_2$ are optionally represented by two linear fits, provided in equations 16 and 17

$$\overline{K_r} \approx -4.03 \cdot SpO_2 - 1.17 \quad (16)$$

$$\overline{K_{ir}} \approx 0.102 \cdot SpO_2 - 0.753 \quad (17)$$

in $mm^2$. The overbar denotes the linear fit of the original function. Referring yet again to the vascular model 814, the pulsatile behavior of $\Delta A_w$, which couples optical detection with the cardiovascular system model, is provided by equation 18, $$\Delta A_w = \frac{A_{w,max}}{\pi} \frac{P_{w,1}}{P_{w,1}^2 + (P_{w,k+1} - P_{w,0})^2} \Delta P_w \quad (18)$$

where $P_{w,0}=(1/3)P_0$ and $P_{w,1}=(1/3)P_1$ account for the poorer compliance of arterioles and capillaries relative to the thoracic aorta. The subscript k is a data index and the subscript k+1 or k+n refers to the next or future data point, respectively.

Referring yet again to the light scattering and absorbance models, third and fourth state variables, the red and infrared reflected intensity ratios, $R=I_{ac}/I_{dc}$, are provided by equations 19 and 20.

$$R_{r,k+1} = c\Sigma_{s,r}' \overline{K_r} \Sigma_{a,r}^{art} \Delta A_w + R_{r,k} + v_r \quad (19)$$

$$R_{ir,k+1} = c\Sigma_{s,ir}' \overline{K_{ir}} \Sigma_{a,ir}^{art} \Delta A_w + R_{ir,k} + v_{ir} \quad (20)$$

Here, v is a process noise, such as an added random number or are Gaussian-distributed process noises intended to capture the baseline wander of the two channels, $\Sigma_{s,r}'$ and $\Sigma_{s,ir}'$ are scattering coefficients, and $\Sigma_{a,r}^{art}$ and $\Sigma_{a,ir}^{art}$ are absorption coefficients.

Sensor Dynamics and Noise Model

The sensor dynamics and noise model 822 is further described. The constant c subsumes all factors common to both wavelengths and is treated as a calibration constant. The observation model adds noises, n, with any probability distribution function to $R_r$ and $R_{ir}$, according to equation 21.

$$\begin{bmatrix} y_{r,k} \\ y_{ir,k} \end{bmatrix} = \begin{bmatrix} R_{r,k} \\ R_{ir,k} \end{bmatrix} + \begin{bmatrix} n_{r,k} \\ n_{ir,k} \end{bmatrix} \quad (21)$$

A calibration constant, c, was used to match the variance of the real $I_{ac}/I_{dc}$ signal with the variance of the dynamic state-space model generated signal for each wavelength. After calibration, the age and gender of the patient was entered. Estimates for the means and covariances of both state and parameter PDFs are optionally entered.

Referring now to FIG. 9, processed data from a relatively high signal-to-noise ratio pulse oximeter data source is provided for about a fifteen second stretch of data. Referring now to FIG. 9A, input photoplethysmographic waveforms are provided. Using the hemodynamics dynamic state-space model 805, the input waveforms were used to extract heart rate (FIG. 9B), left-ventricular stroke volume (FIG. 9C), cardiac output (FIG. 9D), blood oxygen saturation (FIG. 9E), and aortic and systemic (radial) pressure waveforms (FIG. 9F). Several notable points are provided. First, the pulse oximeter provided a first physical value of a hemoglobin oxygen saturation percentage. However, the output blood oxygen saturation percentage, FIG. 9E, was processed by the probabilistic digital signal processor 200. Due to the use of the sensor dynamics and noise model 822 and the spectrometer signal transduction noise model, noisy data, such as due to ambulatory movement of the patient, is removed in the smoothed and filtered output blood oxygen saturation percentage. Second, some pulse oximeters provide a heart rate. However, in this case the heart rate output was calculated using the physical probabilistic digital signal processor 200 in the absence of a heart rate input data source 122. Third, each of the stroke volume, FIG. 9C, cardiac output flow rate, FIG. 9D, aortic blood pressure, FIG. 9E, and radial blood pressure, FIG. 9E, are second physical parameters that are different from the first physical parameter measured by the pulse oximeter photoplethysmographic waveforms.

Referring now to FIG. 10, a second stretch of photoplethysmographic waveforms are provided that represent a low signal-to-noise ratio signal from a pulse oximeter. Low signal-to-noise photoplethysmographic waveforms (FIG. 10A) were used to extract heart rate (FIG. 10B), left-ventricular stroke volume (FIG. 10C), blood oxygen saturation (FIG. 10D), and aortic and systemic (radial) pressure waveforms (FIG. 10E) using the hemodynamics dynamic state-space model 805. In each case, the use of the probabilistic digital signal processor 200 configured with the optional sensor dynamics and noise model 822 and spectrometer signal transduction model 824 overcame the noisy input stream to yield smooth and functional output data for medical use.

The various models relate measurement parameters from a source medical device to a second parameter not measured by the source medical device. For example, an oxygen level is related to a heart stroke volume.

Electrocardiography

Electrocardiography is a noninvasive transthoracic interpretation of the electrical activity of the heart over time as measured by externally positioned skin electrodes. An electrocardiographic device produces an electrocardiogram (ECG or EKG).

The electrocardiographic device operates by detecting and amplifying the electrical changes on the skin that are caused when the heart muscle depolarizes, such as during each heartbeat. At rest, each heart muscle cell has a charge across its outer wall or cell membrane. Reducing the charge toward zero is called de-polarization, which activates the mechanisms in the cell that cause it to contract. During each heartbeat a healthy heart will has orderly progression of a wave of depolarization that is triggered by the cells in the sinoatrial node, spreads out through the atrium, passes through intrinsic conduction pathways, and then spreads all over the ventricles. The conduction is detected as increases and decreases in the voltage between two electrodes placed on either side of the heart. The resulting signal is interpreted in terms of heart health, function, and/or weakness in defined locations of the heart muscles.

Examples of electrocardiograph device lead locations and abbreviations include:
right arm (RA);
left arm (LA);
right leg (RL);
left leg (LL);
in fourth intercostal space to right of sternum ($V_1$);
in fourth intercostal space to left of the sternum ($V_2$);
between leads $V_2$ and $V_4$ ($V_3$);
in the fifth intercostal space in the mid clavicular line ($V_4$);
horizontally even with $V_4$, but in the anterior axillary line ($V_5$); and
horizontally even with $V_4$ and $V_5$ in the midaxillary line ($V_6$).

Usually more than two electrodes are used and they are optionally combined into a number of pairs. For example, electrodes placed at the left arm, right arm, and left leg form the pairs LA+RA, LA+LL, and RA+LL. The output from each pair is known as a lead. Each lead examines the heart from a different angle. Different types of ECGs can be referred to by the number of leads that are recorded, for example 3-lead, 5-lead, or 12-lead ECGs.

Electrocardiograms are used to measure and diagnose abnormal rhythms of the heart, such as abnormal rhythms caused by damage to the conductive tissue that carries electrical signals or abnormal rhythms caused by electrolyte imbalances. In a myocardial infarction (MI) or heart attack, the electrocardiogram is used to identify if the heart muscle has been damaged in specific areas. Notably, traditionally an ECG cannot reliably measure the pumping ability of the heart, for which additional tests are used, such as ultrasound-based echocardiography or nuclear medicine tests. Along with other uses of an electrocardiograph model, the probabilistic mathematical electrocardiograph model, described infra, shows how this limitation is overcome.

EXAMPLE II

A second example of a dynamic state-space model 210 coupled with a dual or joint estimator 222 and/or a probabilistic updater 220 or probabilistic sampler 230 in a medical or biomedical application is provided.

Ischemia and Heart Attack

For clarity, a non-limiting example of prediction of ischemia using an electrocardiograph dynamic state-space model is provided. A normal heart has stationary and homogenous myocardial conducting pathways. Further, a normal heart has stable excitation thresholds resulting in consecutive beats that retrace with good fidelity. In an ischemic heart, conductance bifurcations and irregular thresholds give rise to discontinuous electrophysiological characteristics. These abnormalities have subtle manifestations in the electrocardiograph morphology that persist long before shape of the electrocardiograph deteriorates sufficiently to reach detection by a skilled human operator. Ischemic abnormalities are characterized dynamically by non-stationary variability between heart beats, which are difficult to detect, especially when masked by high frequency noise, or similarly non-stationary artifact noise, such as electrode lead perturbations induced by patient motion.

Detection performance is improved substantially relative to the best practitioners and current state-of-the-art algorithms by integrating a mathematical model of the heart with accurate and rigorous handling of probabilities. An example of an algorithm for real time and near-optimal ECG processing is the combination of a sequential Monte Carlo algorithm with Bayes rule. Generally, an electrodynamic mathematical model of the heart with wave propagation through the body is used to provide a "ground truth" for the measured signal from the electrocardiograph electrode leads. Use of a sequential Monte Carlo algorithm predicts a multiplicity of candidate values for the signal, as well as other health states, at each time point, and each is used as a prior to calculate the truth estimate based on sensor input via a Bayesian update rule. Since the model is electrodynamic and contains state and model parameter variables corresponding to a normal condition and an ischemic condition, such events can be discriminated by the electrocardiograph model, described infra.

Unlike simple filters and algorithms, the electrocardiograph dynamic state-space model coupled with the probabilistic updater 220 or probabilistic sampler 230 is operable without the use of assumptions about the regularity of morphological variation, spectra of noise or artifact, or the linearity of the heart electrodynamic system. Instead, the dynamic response of the normal or ischemic heart arises naturally in the context of the model during the measurement process. The accurate and rigorous handling of probabilities of this algorithm allows the lowest possible detection limit and false positive alarm rate at any level of noise and/or artifact corruption.

Electrocardiograph with Probabilistic Data Processing

Figure 11:
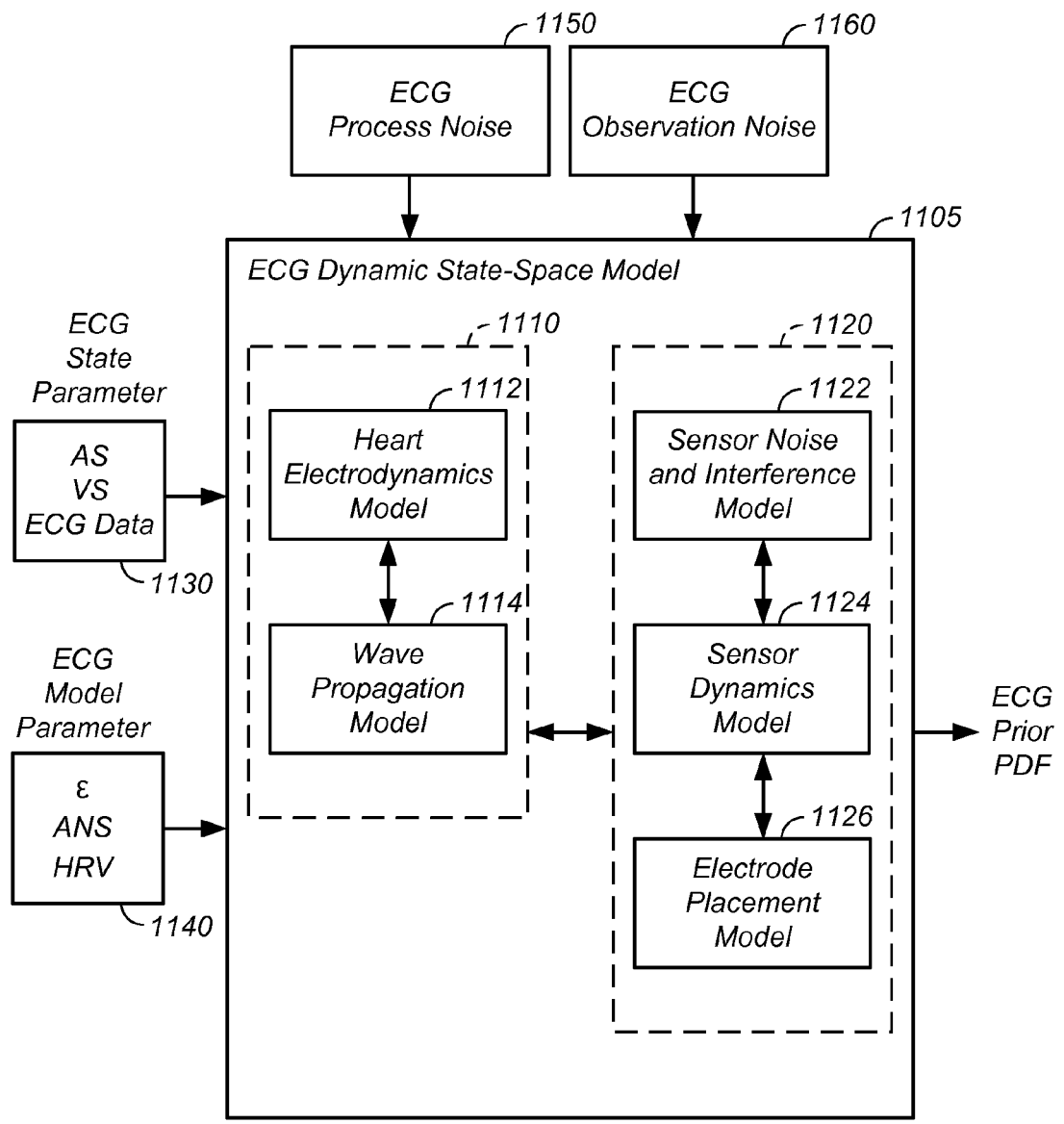
FIG. 11 is a flow chart showing the components of a electrocardiograph dynamic state-space model.

FIG. 11 is a schematic of an electrocardiograph dynamic state-space model suitable for processing electrocardiogram data, including components required to describe the processes occurring in a subject. The combination of SPKF or SMC filtering in state, joint, or dual estimation modes is optionally used to filter electrocardiograph (ECG) data. Any physiology model adequately describing the ECG signal is optionally used, as well as any model of noise and artifact sources interfering or contaminating the signal. One non-limiting example of such a model is a model using a sum of arbitrary wave functions with amplitude, center and width, respectively, for each wave (P, Q, R, S, T) in an ECG. The observation model comprises the state plus additive Gaussian noise, but more realistic pink noise or any other noise probability distributions is optionally used.

Still referring to FIG. 11, to facilitate description of the electrocardiograph dynamic state-space model 1105, a non-limiting example is provided. In this example, the electrocardiograph dynamic state-space model 1105 is further described. The electrocardiograph dynamic state-space model 1105 preferably includes a heart electrodynamics model 1110 corresponding to the dynamic state-space model 210 process model 710. Further, the electrocardiograph dynamic state-space model 1105 preferably includes a heart electrodynamics observation model 1120 corresponding to the dynamic state-space model 210 observation model 720. The electrocardiograph process model 1110 and electrocardiogram observation model 1120 are further described, infra.

Still referring to FIG. 11, the electrocardiograph process model 1110 optionally includes one or more of a heart electrodynamics model 1112 and a wave propagation model 1114. The heart electrodynamics model 1112 is a physics based model of the electrical output of the heart. The wave propagation model 1114 is a physics based model of movement of the electrical pulses through the lungs, fat, muscle, and skin. An example of a wave propagation model 1114 is a thorax wave propagation model modeling electrical wave movement in the chest, such as through an organ. The various models optionally share information. For example, the electrical pulse of the heart electrodynamics model 1112 is optionally an input to the wave propagation model 1114, such as related to one or more multi-lead ECG signals. Generally, the process model 710 components are optionally probabilistic, but are preferentially deterministic. Generally, the observation model 720 components are probabilistic.

Still referring to FIG. 11, the electrocardiogram observation model 1120 optionally includes one or more of a sensor noise and interference model 1122, a sensor dynamics model 1124, and/or an electrode placement model 1126. Each of the sensor noise and interference model 1122 and the sensor dynamics models 1124 are optionally physics based probabilistic models related to noises associated with the instrumentation used to collect data, environmental influences on the collected data, and/or noise due to the human interaction with the instrumentation, such as movement of the sensor. A physics based model uses at least one equation relating forces, electric fields, pressures, or light intensity to sensor provided data. The electrode placement model 1126 relates to placement of the electrocardiograph leads on the body, such as on the arm, leg, or chest. As with the electrocardiograph process model 1110, the sub-models of the electrocardiograph observation model 1120 optionally share information. For instance, a first source of noise, such as sensor noise related to movement of the sensor, is added to a second source of noise, such as a signal transduction noise. Optionally and preferably, the electrocardiograph observation model 1120 shares information with and/provides information to the electrocardiograph process model 1110.

The electrocardiograph dynamic state-space model 1105 receives inputs, such as one or more of:
  electrocardiograph state parameters 1130;
  electrocardiograph model parameters 1140;
  electrocardiograph process noise 1150; and
  electrocardiograph observation noise 1160.

Examples of electrocardiograph state parameters 1130, corresponding to state parameters 730, include: atrium signals (AS), ventricle signals (VS) and/or ECG lead data. Examples of electrocardiograph model parameters 1140, corresponding to the more generic model parameters 740, include: permittivity, $\epsilon$, autonomic nervous system (ANS) tone or visceral nervous system, and a heart rate variability (HRV). Heart rate variability (HRV) is a physiological phenomenon where the time interval between heart beats varies and is measured by the variation in the beat-to-beat interval. Heart rate variability is also referred to as heart period variability, cycle length variability, and RR variability, where R is a point corresponding to the peak of the QRS complex of the electrocardiogram wave and RR is the interval between successive Rs. In this example, the output of the electrocardiograph dynamic state-space model 1105 is a prior probability distribution function with parameters of one or more of the input electrocardiograph state parameters 1130 after operation on by the heart electrodynamics model 1112, a static number, a probability function, and/or a parameter not measured or output by the sensor data.

An example of an electrocardiograph with probabilistic data processing is provided as an example of the electrocardiogram dynamic state-space model 1105. The model is suitable for processing data from an electrocardiograph. In this example, particular equations are used to further describe the electrocardiograph dynamic state-space model 1105, but the equations are illustrative and non-limiting in nature.

Heart Electrodynamics

The heart electrodynamics model 1112 of the ECG dynamic state-space model 1105 is further described. The transmembrane potential wave propagation in the heart is optionally simulated using Fitz Hugh-Nagumo equations. The heart model 1112 is optionally implemented, for instance, as a coarse-grained three-dimensional heart anatomical model or as a compartmental, zero-dimensional model of the heart. The latter could take the form, for instance, of separate atrium and ventricle compartments.

In a first example of a heart electrodynamics model 1112, a first set of equations for cardiac electrodynamics are provided by equations 22 and 23, $$\dot{u} = div(D \nabla u) + ku(1-u)(u-a) - uz \quad (22)$$

$$\dot{z} = -\left(e + \frac{u_1 z}{u + u_2}\right)(ku(u - a - 1) + z) \quad (23)$$

where D is the conductivity, u is a normalized transmembrane potential, and z is a secondary variable for the repolarization. In the compartmental model, $u_i$ becomes either the atrium potential, $u_{as}$, or the ventricle potential, $u_{vs}$. The repolarization is controlled by k and e, while the stimulation threshold and the reaction phenomenon is controlled by the value of a. The parameters $_1$ and $_2$ are preferably empirically fitted.

A second example of a heart electrodynamics model is presented, which those skilled in the art will understand is related to the first heart electrodynamics model. The second heart electrodynamics model is expanded to include a restitution property of cardiac tissue, where restitution refers to a return to an original physical condition, such as after elastic deformation of heart tissue. The second heart electrodynamics model is particularly suited to whole heart modeling and is configured for effectiveness in computer simulations or models.

The second heart electrodynamics model includes two equations, equations 24 and 25, describing fast and slow processes and is useful in adequately representing the shape of heart action potential, $$\frac{\partial u}{\partial t} = \frac{\partial}{\partial x_i} d_{ij} \frac{\partial u}{\partial x_j} - ku(u-a)(u-1) - uv \quad (24)$$

$$\frac{\partial v}{\partial t} = \varepsilon(u,v)(-v - ku(u-a-1)) \quad (25)$$

where $\epsilon(u,v)=\epsilon_0+u_1 v/(u+u_2)$. Herein, the approximate values of k=8, a=0.15, and $\epsilon_0$=0.002 are used, but the values are optionally set for a particular model. The parameters $u_1$ and $u_2$ are set for a given model and $d_{ij}$ is the conductivity tensor accounting for the heart tissue anisotropy.

Further, the second heart electrodynamics model involves dimensionless variables, such as u, v, and t. The actual transmembrane potential, E, and time, t, are obtained using equations 26 and 27 or equivalent formulas.

$$e[mV]=100u-80 \quad (26)$$

$$t[ms]=12.9t[t.u.] \quad (27)$$

In this particular case, the rest potential $E_{rest}$ is about -80 mV and the amplitude of the pulse is about 100 mV. Time is scaled assuming a duration of the action potential, APD, measured at the level of about ninety percent of repolarization, $APD_0$=330 ms. The nonlinear function for the fast variable u optionally has a cubic shape.

The dependence of $\epsilon$ on u and v allows the tuning of the restitution curve to experimentally determined values using $u_1$ and $u_2$. The shape of the restitution curve is approximated by equation 28, $$APD = \frac{CL}{(aCL+b)} \quad (28)$$

where the duration of the action potential, APD, is related to the cycle length, CL. In dimensionless form, equation 28 is rewritten according to equation 29, $$\frac{1}{apd} = 1 + \frac{b}{cl} \quad (29)$$

where apd=APD/$APD_0$, and $APD_0$ denotes APD of a free propagating pulse.

Restitution curves with varying values of parameters $u_1$ and $u_2$ are used, however, optional values for parameters $u_1$ and $u_2$ are about $u_1$=0.2 and $u_2$=0.3. One form of a restitution curve is a plot of apd vs. cl, or an equivalent. Since a restitution plot using apd vs. cl is a curved line, a linear equivalent is typically preferred. For example, restitution curve is well fit by a straight line according to equation 30.

$$\frac{1}{apd} = k_1 + \frac{k_2}{cl} \quad (30)$$

Optional values of $k_1$ and $k_2$ are about 1.0 and 1.05, respectively, but are preferably fit to real data for a particular model. Generally, the parameter $k_2$ is the slope of the line and reflects the restitution at larger values of CL.

The use of the electrodynamics equations, the restitutions, and/or the restitution curve is subsequently used to predict or measure arrhythmia. Homogeneous output is normal. Inhomogeneous output indicates a bifurcation or break in the conductivity of the heart tissue, which has an anisotropic profile, and is indicative of an arrhythmia. Hence, the slope or shape of the restitution curve is used to detect arrhythmia.

Wave Propagation

The electric wave model 1114 of the ECG dynamic state-space model 1105 is further described. The propagation of the heart electrical impulse through lung and other tissues before reaching the sensing electrodes is optionally calculated using Gauss' Law, $$\nabla \cdot E(t) = \frac{u_i(t)}{\varepsilon_0} \quad (31)$$

where $_i(t)$ is the time-varying charge density given by the heart electrodynamics model and $\epsilon_0$ is the permittivity of free space, which is optionally scaled to an average tissue permittivity.

Sensor Dynamics

The sensor dynamics model 1124 of the ECG dynamic state-space model 1105 is further described. The ECG sensor is an electrode that is usually interfaced by a conducting gel to the skin. When done correctly, there is little impedance from the interface and the wave propagates toward a voltage readout. The overall effect of ancillary electronics on the measurement should be small. The relationship between the wave and readout can be written in general as:

$$V(t)=G(E(t))+N(p)+D(s,c) \quad (32)$$

where G is the map from the electrical field reaching the electrode and voltage readout. This includes the effect of electronics and electrode response timescales, where N is the sensor noise and interference model and D is the electrode placement model.

Sensor Noise and Interference Model

The sensor noise and interference model 1122 of the ECG dynamic state-space model 1105 is further described. The sensor noise enters the DSSM as a stochastic term (Langevin) that is typically additive but with a PDF that is both non-Gaussian and non-stationary. Optionally non-stationarity is modeled from the perturbation, p, representing both external interference and cross-talk. One way to accomplish this is to write:

$$N(E(t),p)=\alpha n_1+\beta p n_2 \quad (33)$$

where alpha, $\alpha$, and beta, $\beta$, are empirical constants and $n_1$ and $n_2$ are stochastic parameters with a given probability distribution function.

Electrode Placement Model

The electrode placement model 1126 of the ECG dynamic state-space model 1105 is further described. This model is an anatomical correction term to the readout equation operating on the sagittal and coronal coordinates, s and c, respectively. This model varies significantly based on distance to the heart and anatomical structures between the heart and sensor. For instance, the right arm placement is vastly different than the fourth intercostal.

Optionally, the output from the electrocardiograph probabilistic model is an updated, error filtered, or smoothed version of the original input data. For example, the probabilistic processor uses a physical model where the output of the model processes low signal-to-noise ratio events to yield any of: an arrhythmia detection, arrhythmia monitoring, an early arrhythmia warning, an ischemia warning, and/or a heart attack prediction.

Optionally, the model compares shape of the ECG with a reference look-up table, uses an intelligent system, and/or uses an expert system to estimate, predict, or produce one or more of: an arrhythmia detection, an ischemia warning, and/or a heart attack warning.

Figure 13A:
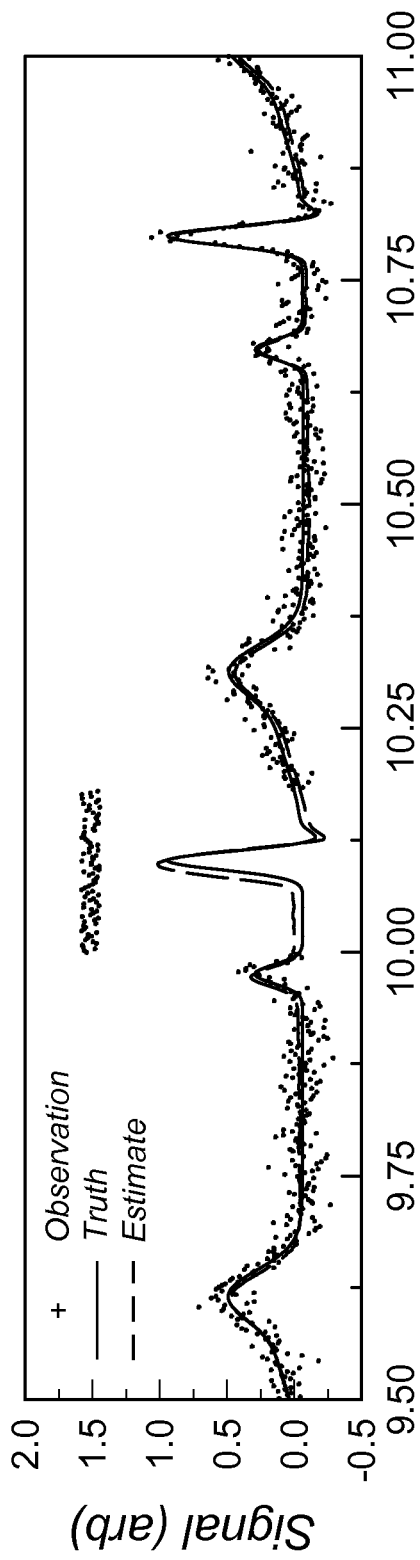
FIG. 13A and FIG. 13B are charts showing input ECG sensor data and comparing output data from a data processor according to the present invention with output data generating using a Savitzky-Golay FIR data processing algorithm.
Figure 13B:
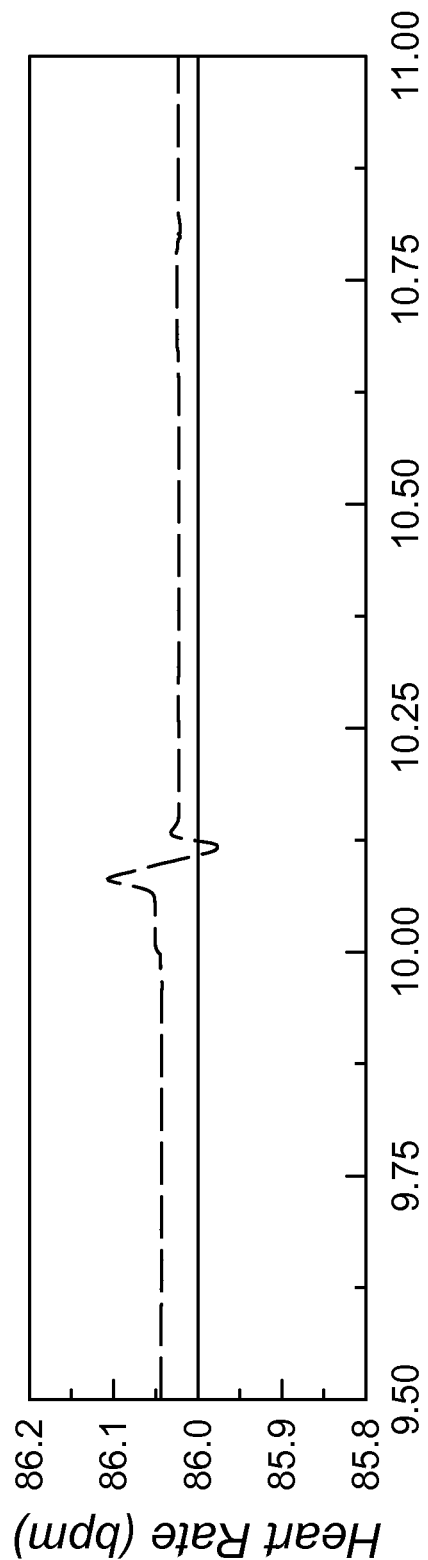

Referring now to FIG. 12A and FIG. 12B, the results of processing noisy non-stationary ECG signals are shown. Heart rate oscillations representative of normal respiratory sinus arrhythmia are present in the ECG. The processor accomplishes accurate, simultaneous estimation of the true ECG signal and a heart rate that follows closely the true values. Referring now to FIG. 13A and FIG. 13B, the performance of the processor using a noise and artifact-corrupted signal is shown. A clean ECG signal representing one heart beat was contaminated with additive noise and an artifact in the form of a plateau at R and S peaks (beginning at time=10 sec). Estimates by the processor remain close to the true signal despite the noise and artifact.

Fusion Model

Optionally, inputs from multiple data sources, such as sensors or medical instruments, are fused and used in the probabilistic digital signal processor 200. The fused data often include partially overlapping information, which is shared between models, used in a fused model, and/or is used in a global model to enhance parameter estimation. The overlapping information results in benefits of the fused model, including:
- enhanced accuracy of an estimated parameter;
- enhanced precision of an estimated parameter;
- noise artifact reduction in a data stream; and/or
- an additionally determined metric.

Herein, fusion of data from biomedical sensors is used to illustrate the benefits of sensors fusion in combination with a physical model. However, the concept extends to cover mechanical systems using sensors.

Data Fusion

Figure 14:
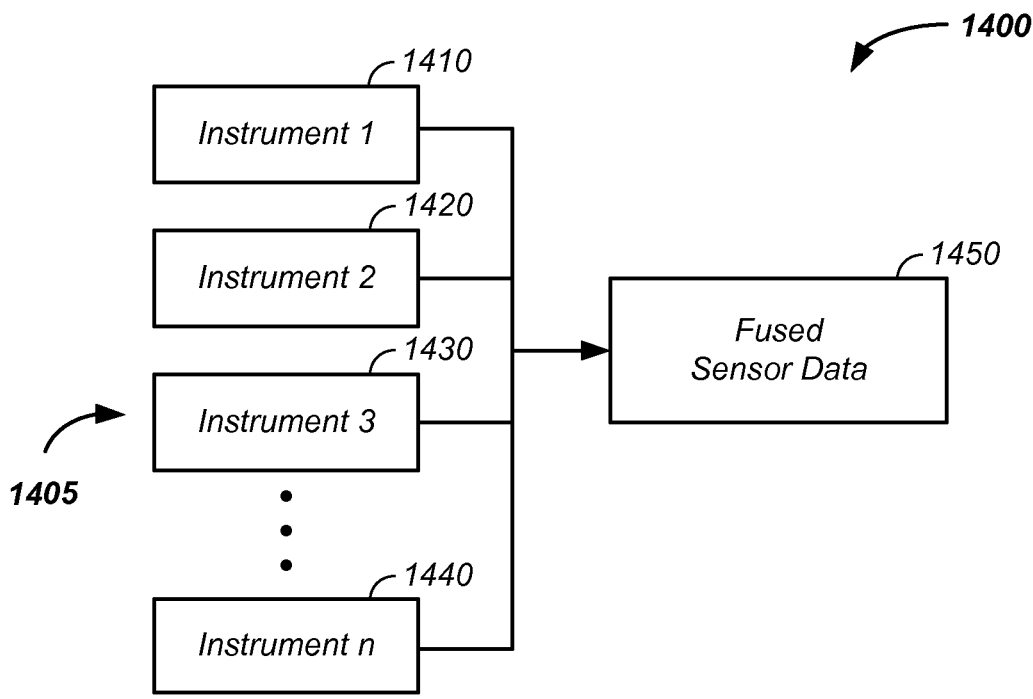
FIG. 14 illustrates fusion of data from multiple instruments.

Referring now to FIG. 14, an overview of a sensor fusion system 1400 in combination with at least one physical model and a probabilistic processor 200 is provided. Generally, data from multiple instruments 1405 is provided to the probabilistic processor 200, such as to the probabilistic updater 220, dual or joint estimator 222, state parameter updater 224, and/or the model parameter updater 226. More particularly, data from a first instrument 1410, second instrument 1420, third instrument 1430, and/or n$^{th}$ instrument 1440 is provided to the probabilistic processor 200, where n is a positive integer, such as at least 2, 3, 4, or 5. One or more of the n instruments 1405 optionally include readings from multiple sensors. As a first example, if the first instrument 1410 is a pulse oximeter, then output from the pulse oximeter as input to the probabilistic processor 200 optionally includes one or more of: raw sensor data, voltage data, processed spectral intensity data, or pulse oximeter generated output data, such as a blood oxygen saturation percentage. As a second example, if the second instrument 1420 is an electrocardiograph device, then output from the electrocardiograph device as input to the probabilistic processor 200 optionally includes one or more of: raw sensor data, current, voltage, resistance, processed electrocardiograph device signal, and/or an outcome, such as an indication of a previous heart attack. In a third example, output from an instrument includes environmental information, such as temperature, pressure, vibration, and humidity. Herein, time readings are optionally input along with any of the sensor data from any of the multiple instruments 1405, but time is not considered a sensed value nor does time count as one of the multiple data sources fused with the probabilistic processor 200. The fused sensor data 1450 refers to any form, matrix, concatenation, combination, union, representation, or mathematical combination of the data from the multiple instruments 1405. The fused sensor data 1450 is preferably fused by use of the probabilistic processor 200 but is optionally fused prior to input into the probabilistic processor 200.

Figure 15:
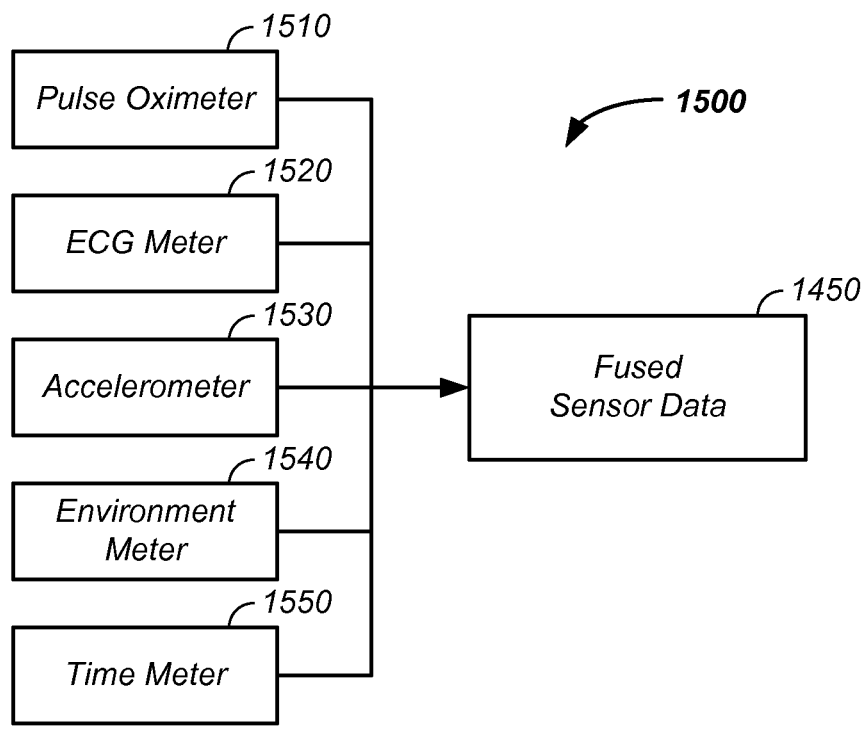
FIG. 15 illustrates fusion of biomedical data, accelerometer data, and/or environmental data.

Referring now to FIG. 15, an example of a pulse oximeter 1510 and an electrocardiograph meter or device 1520 used as inputs to the probabilistic processor 200 is provided. The pulse oximeter 1510 provides time dependent values to the probabilistic processor 200, such as raw sensor data, voltage data, processed spectral intensity data, or pulse oximeter generated output data, such as a blood oxygen saturation percentage. The electrocardiograph meter 1520 additionally provides time dependent values to the probabilistic processor 200, such as raw sensor data, current, voltage, resistance, processed electrocardiograph device signal, and/or an outcome, such as a previous heart attack indication. The pulse oximeter 1510 data and electrocardiograph device 1520 data are optionally fused, as described supra. As discussed, infra, additional input data is provided to the probabilistic processor 200, such as data from an accelerometer 1530, data from a time meter 1550, and/or data from an environment meter 1540, such as temperature, pressure, vibration, humidity, and/or position information. The data is at least partially fused into fused sensor data 1450, as described supra.

Integration of Fused Data with Probabilistic Processor

Figure 16:
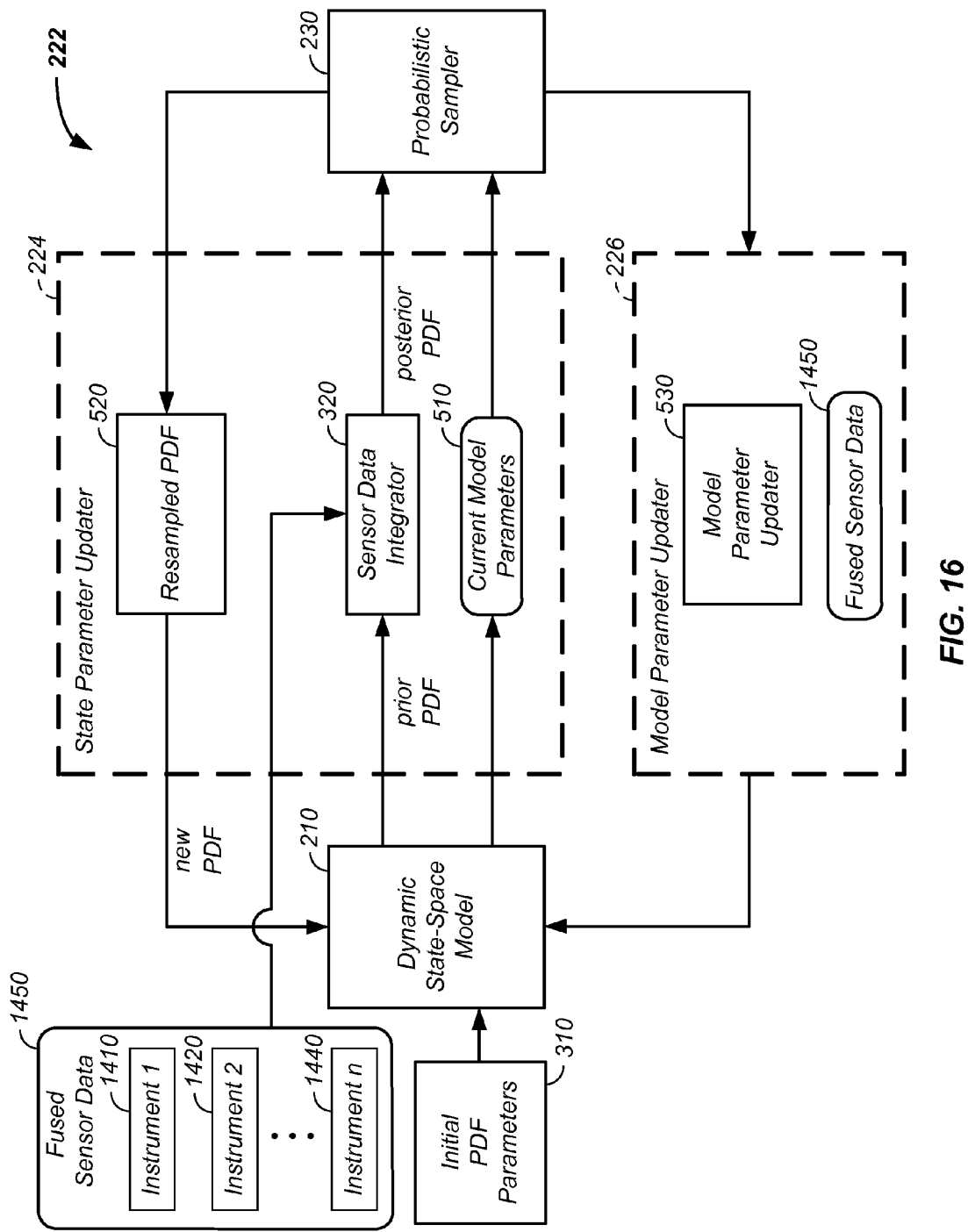
FIG. 16 shows integration of multiple data streams into a joint processor.

Referring now to FIG. 16, an example of data originating from the multiple instruments 1405 as input to the dual or joint estimator 222 is provided. As illustrated, the data from the multiple instruments 1405, described supra, is optionally input into the state parameter updater 224 or into the model parameter updater 226. As described, supra, the data from the multiple instruments 1405 is optionally fused prior to and/or after entry into any of the probabilistic processor 200 subcomponents or software algorithms. Similarly, the initial probability distribution function parameters 310 optionally include initial values/probabilities for each of the multiple instruments 1405.

Fusion Configured Dynamic State-Space Model

Figure 17:
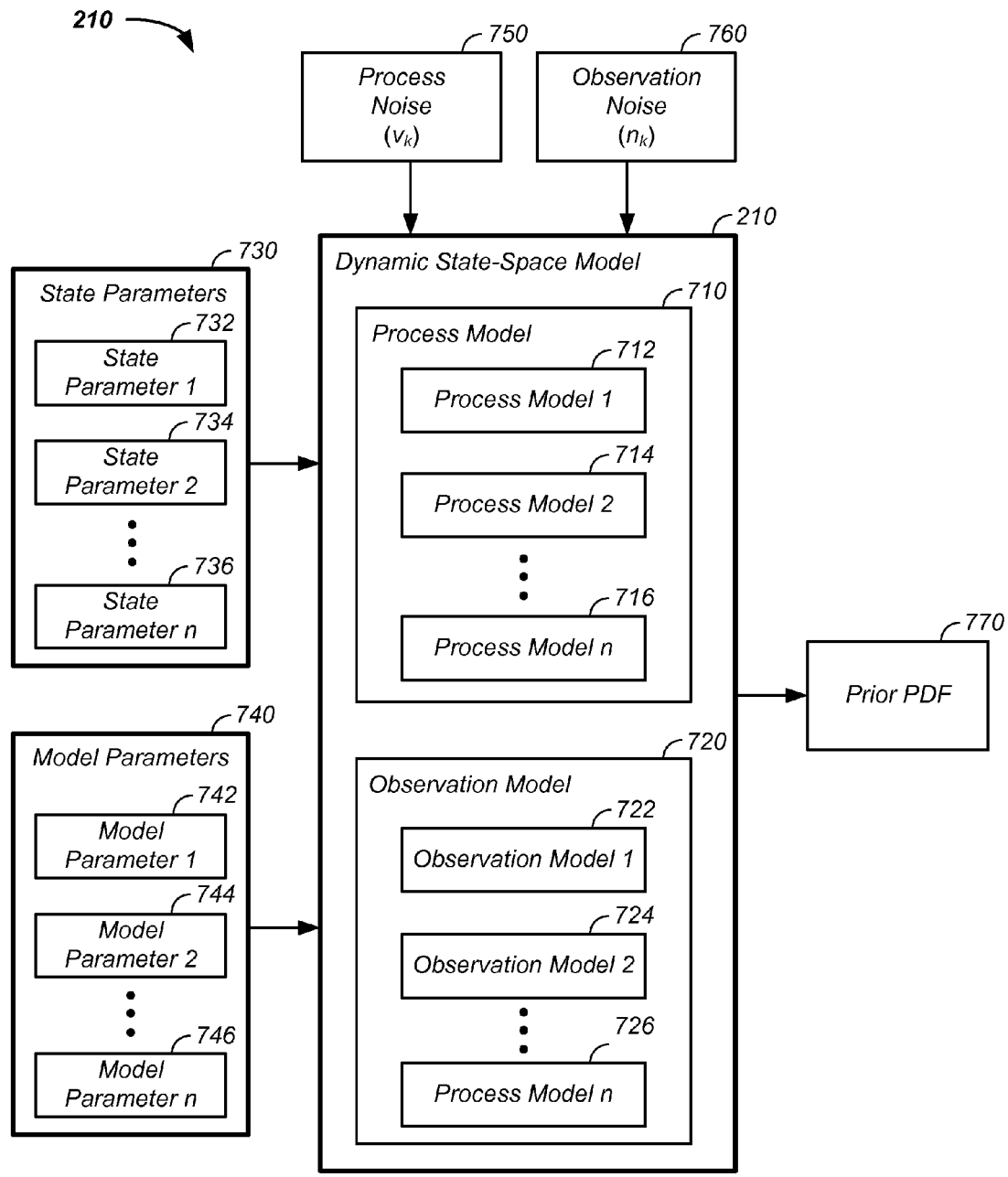
FIG. 17 illustrates a fusion dynamic state-space model.

Referring now to FIG. 17, an example of a dynamic state-space model 210 configured for use with data from the multiple instruments 1405 is provided.

Process Model

For example, the process model 710 of the dynamic state-space model 210, optionally includes a first process model 712 related to data from the first instrument 1410 and a second process model 714 configured to use and represent data from the second instrument 1420. Generally, there are about n process models 716 related to the n instruments 1440, though 1, 2, 3, or more process models are optionally configured to represent or process the data from the n instruments.

Observation Model

Similarly, the observation model 720 of the dynamic state-space model 210, optionally includes a first observation model 722 related to data from the first instrument 1410 and a second observation model 724 configured to use and represent data from the second instrument 1420. Generally, there are about n observation models 716 related to the n instruments 1440, though 1, 2, 3, or more observation models are optionally configured to represent or process the data from the n instruments.

State and Model Parameters

The dynamic state-space model optionally receives state parameter 730 inputs. Examples of DSSM inputs include:
- a first state parameter 732, such as a parameter from the first instrument 1410;
- a second state parameter 734, such as a value measured by the second instrument 1420; and
- an $n^{th}$ state parameter 736, such as a parameter determined by the dynamic state-space model 210.

Similarly, the dynamic state-space model 210 optionally receives model parameter 740 inputs. Examples of model parameter inputs include:
- a first model parameter 742, such as a parameter from the first instrument 1410;
- a second model parameter 744, such as a modeled value; and
- an $n^{th}$ state parameter 746, such as a parameter determined by the dynamic state-space model 210.

The dynamic state-space model 210 optionally receives fusion process noise 750 input and/or fusion observation noise 760 input.

Pulse Oximeter/Electrocardiograph Fusion

The non-limiting example of fusion of information from a pulse oximeter and an electrocardiogram device is further described to clarify model fusion and/or information combination.

A pulse oximeter and an electrocardiograph meter both provide information on the heart. Hence, the pulse oximeter and the electrocardiograph meter provide overlapping information, which is optionally shared, such as between the hemodynamics dynamic state-space model 805 and the electrocardiogram dynamic state-space model 1105. Similarly, a fused model incorporating aspects of both the hemodynamics dynamic state-space model 805 and the electrocardiogram dynamic state-space model 1105 is created, which is an example of a fused model. Particularly, in an electrocardiogram the left-ventricular stroke volume is related to the power spent during systolic contraction, which is, in turn, related to the electrical impulse delivered to that region of the heart. Indeed, the R-wave amplitude is optionally correlated to contractility. It is readily seen that other features of the electrocardiogram also have relationships with the cardiac output function. As described, supra, the pulse oximeter also provides information on contractility, such as heart rate, stroke volume, cardiac output flow rate, and/or blood oxygen saturation information. Since information in common is present, the system is over determined, which allows outlier analysis and/or calculation of a heart state or parameter with increased accuracy and/or precision.

Figure 18:
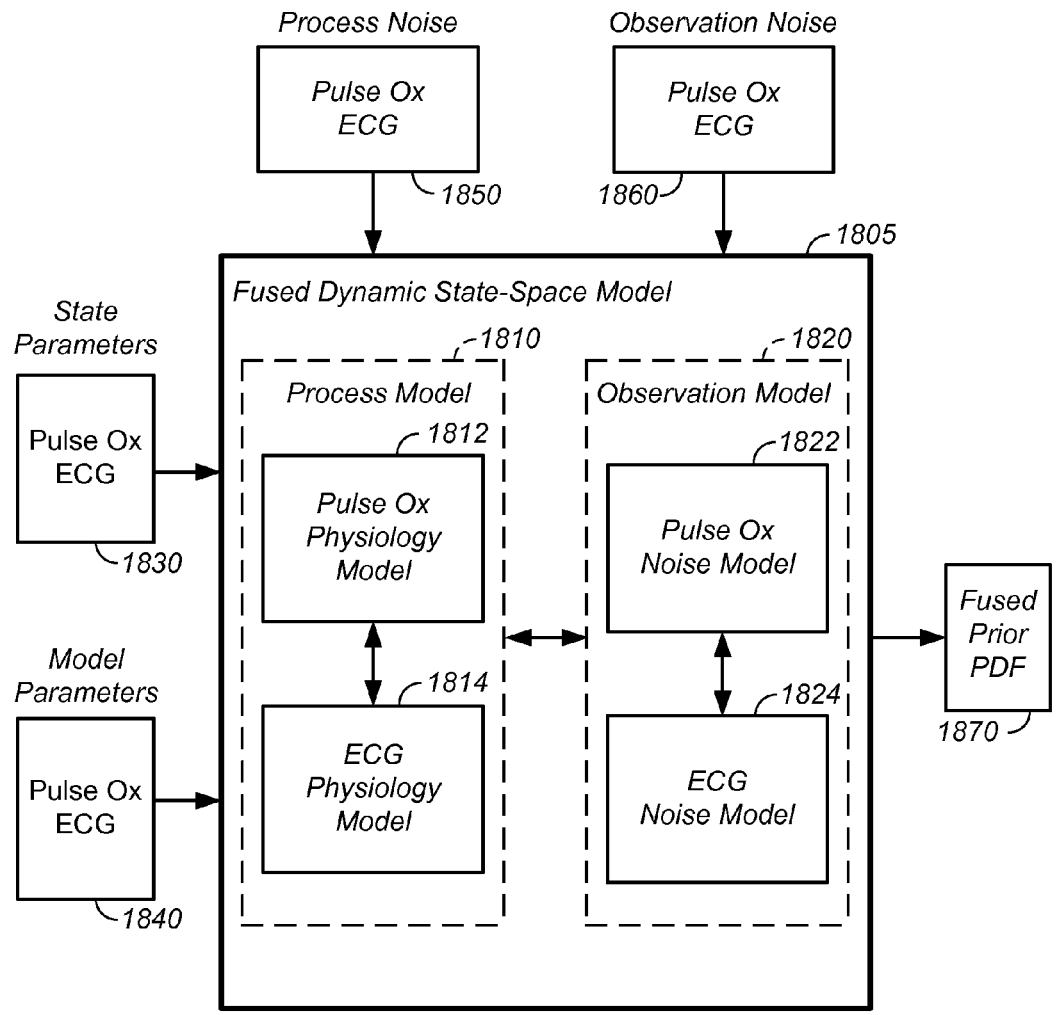
FIG. 18 illustrates combination of medical data streams into a physics based model.

Referring now to FIG. 18, a particular example of a fused dynamic state-space model 1805 is presented. In this example, output from a traditional pulse oximeter 1510 is fused with output from a traditional electrocardiogram device 1520. In this example, the fused dynamic state-space model 1805 incorporates models covering both hemodynamics and heart electrodynamics. Generally, a fused dynamic state-space model 1805 incorporates one or more models modeling information from the multiple instruments 1405.

In this example, a fused process model 1810, of the fused dynamic state-space model 1805, includes one or more of a pulse oximeter physiology process model 1812, the hemodynamics process model 810, an electrocardiograph physiology model 1814, and/or the heart electrodynamics model 1110. For instance, the pulse oximeter physiology process model 1812 optionally incorporates one or more of the hemodynamics heart model 812, the hemodynamics vascular model 814, and/or the light scattering and/or absorbance model 816. Similarly, the electrocardiogram physiology process model 1814 optionally incorporates one or more of the heart electrodynamics model 1112 and/or the wave propagation model 1114.

In this example, a fused observation model 1820, of the fused dynamic state-space model 1805, includes one or more of a pulse oximeter observation noise model 1822, the hemodynamics observation model 820, an electrocardiograph noise model 1824, and/or the electrodynamics observation model 1120. For instance, the pulse oximeter observation noise model 1822 optionally incorporates one or more of the sensor dynamics and noise model 822 and the spectrometer signal transduction noise model 824. Similarly, the electrocardiograph observation noise model 1824 optionally incorporates one or more of the sensor noise and interference model 1122, the sensor dynamics model 1124, and/or the electrode placement model 1126. Any of the process model 1810 sub-models, such as the pulse oximeter physiology model 1812 and electrocardiogram physiology model 1814 share information or data with any of: another process model 1810 sub-model, the process model 1810, the observation model 1820, or any observation model 1820 sub-model, such as the pulse oximeter model 1822 and/or the electrocardiogram noise model 1824.

Generally, in a fused dynamic state-space model, the process model and observation model are optionally combined into a single model or are separate and share information. Further, any sub-model of the process model or sub-model of the observation model shares information or data with any other sub-model of the process model or observation model.

As described, supra, for the dynamic state-space model 210, the fused dynamic state-space model 1805 for the heart optionally receives inputs, including one or more of:
- pulse oximeter and electrocardiograph device state parameters 1830;
- pulse oximeter and electrocardiograph device model parameters 1840;
- pulse oximeter and electrocardiograph device process noise values 1850; and
- pulse oximeter and electrocardiograph device observation noise values 1860.

For example, the pulse oximeter and electrocardiograph device state parameters 1830 optionally include one or more of:
- pulse oximeter related values of:
  - a radial pressure ($P_w$);
  - an aortic pressure ($P_{ao}$);
  - time (t);
  - a spectral intensity (I) or a related absorbance value;
  - a reflectance or reflectance ratio, such as a red reflectance ($R_r$) or an infrared reflectance ($R_{ir}$); and/or
  - a spectral intensity ratio ($I_R$); and
- electrocardiograph device related values of:
  - an atrium signal (AS); and/or
  - a ventricle signal (VS).

In another example, the electrocardiograph device observation parameters 1840 optionally include one or more of:
- pulse oximeter related values of:
  - a heart rate (HR);
  - a stroke volume (SV); and/or
  - a whole-blood oxygen saturation ($SpO_2$); and
- electrocardiograph device related values of:
  - a permittivity, ($\epsilon$);
  - an autonomic nervous system (ANS) tone; and/or
  - a heart rate variability (HRV).

Fusion Benefits

Several non-limiting examples of the benefits of sensor fusion using at least one physiological model and a probabilistic processor 200 are provided.

Stroke Volume and Contractility

In a first case, fused, fusion, or fusing of sensor data from multiple instruments in combination with physical models of body systems yields additional information not present from any given instrument of the multiple instruments 1405. Without loss of generality, an example of generating a measure of stroke volume, a contractility, and/or a heart filling rate using data from a pulse oximeter and an electrocardiograph meter is used to demonstrate the indirect parameter estimation.

Herein, benefits of combining hemodynamic information with electrodynamic information in a fusion model is described. As described, supra, a pulse oximeter plethysmograph in combination with a hemodynamics physical model is used to determine a physical parameter not traditionally achieved from the pulse oximeter, such as a heartbeat stroke volume. Similarly, as described, supra, an electrocardiogram in combination with an electrodynamics physical model is used to determine a physical parameter not traditionally achieved from the electrocardiograph meter, such as contractility. Stroke volume and contractility are related, such as according to equation 34, $$SV \approx FR \cdot C \quad (34)$$

where SV is stroke volume, FR, is the heart filing rate, and C is contractility. Here, the filling rate is determined using information indirectly measured by two systems (SV from the pulse oximeter and C from the ECG). Further, given a known or approximated filling rate, the electrocardiogram determined contractility gives information on the pulse oximeter determined stroke volume, and vise-versa.

In another case, fusing sensor data results in increased information for parameters determined with individual sensor data when the sensed data overlaps in terms of physiology and/or models thereof. For example, as stroke volume is an element of the heart model 812, which is tied to additional hemodynamic models in the hemodynamics dynamic state-space model, such as the vascular model 814, and the stroke volume is related to electrocardiograph data, as described supra, then the electrocardiograph signal optionally aids in determination of parameters directly or indirectly measured by the pulse oximeter and vise-versa. Generally, the electrodynamic signal is related to the hemodynamic signal through the use of one or more models, such as the hemodynamics dynamic state-space model 805, the electrocardiograph dynamic state-space model 1105, or a heart model combining two or more elements of the hemodynamics DSSM model 805 and the electrocardiograph DSSM model 1105.

Arrhythmia

As described, supra, in some systems, such as the heart, hemodynamic information and electrodynamic information are related. As described, supra, the hemodynamic information of stroke volume is related to the electrodynamic information of contractility. Hence, the hemodynamic information of the pulse oximeter yields additional information to any of the parameters measured by the electrocardiogram, such as an arrhythmia. Logically, if the heart is experiencing an arrhythmia, which is being detected by the electrocardiogram probabilistic model, then the heart is experiencing diminished stroke volume, as detected by the pulse oximeter. Hence, the hemodynamic information originating with the pulse oximeter provides supporting or combinatorial information to the electrocardiograph probabilistic model.

Similarly, a blood pressure meter yields information on blood pressure, which is related to heart function. Hence, blood pressure meter information is synergistic with electrocardiograph information and vise-versa. Further, blood pressure meter information is synergistic with hemodynamic, photoplethysmograph, and/or pulse oximeter information and vise-versa Motion Artifact In yet another example, patient movement results in a motion artifact in the sensed data of a given sensor. In many of the observation models 720 of the dynamic state-space model 210, a model is used that relates to sensor movement and/or movement of the body. As a first example, the hemodynamics dynamic state-space model 805 optionally uses the hemodynamics sensor dynamics and noise model 822. As a second example, the electrocardiogram dynamic state-space model 1105 optionally uses the sensor dynamic model 1124. Each of these models relate to movement of the sensor relative to the sensed element, such as the body. Hence, if the body moves, twitches, and/or experiences a bump in transport, such as in transport by an ambulance, the body movement may be detected as a motion artifact with a plurality of sensors. For example, the pulse oximeter and the electrocardiograph device may each detect the same motion artifact. Hence, fusion of the sensed data from multiple instruments allows the identification of an outlier signal or motion artifact signal in data from a first sensor through detection of the same motion artifact with a second sensor. Therefore, identification of a motion artifact with a first sensor is used to remove the same motion artifact from data from a second sensor. Optionally, an accelerometer is used to detect motion artifacts. The fusion of input sensor data from the accelerometer with data streams from one, two, or more additional devices allows removal of the motion artifact data from the one, two, or more additional devices.

Heart Rate Variability

In another example, sensor fusion is used to enhance a measure of heart rate variability. Generally, use of multiple sensors yields: (1) an over-determined system for outlier analysis and/or (2) varying sensor types where not all of the sensors are affected by a noise source. Herein, heart rate variability or variation in beat-to-beat interval of a heart is used to demonstrate each of these cases.

Heart rate variability is measured using a blood pressure meter, a photoplethysmograph derived from a pulse oximeter, or an electrocardiogram device. However, each of the blood pressure meter, pulse oximeter, and electrocardiogram device are subject to noise and/or patient motion artifacts, which result in false positive heartbeats and/or missed heartbeats.

Using a combination of sensors, such as the blood pressure meter, pulse oximeter, and/or electrocardiogram device, results in an over-determined system. The over-determined system allows for outlier analysis. By fusing the signals, an ambiguous signal from the first device is detected and overcome by use of the signal from the second measuring device.

Further, noise sources affecting a first measuring device, such as a pulse oximeter, are often separate from noise sources affecting a second measuring device, such as an electrocardiogram meter. For instance, electrical interference may affect an electrodynamic signal, such as the electrocardiograph, while not impacting a hemodynamic signal, such as a photoplethysmograph. By fusing the signals, noise is recognized in one sensor data stream at a given time as the noise source is not present in the second sensor data stream at the same time due to the noise source type not affecting both sensor types.

Environment Meter

In still yet another case, sensor output from one, two, or more instruments is additionally fused with output from an environmental meter. Herein, an environment meter senses one or more of: temperature, pressure, vibration, humidity, and/or position information, such as from a global positioning system. The environment meter information is used for outlier determination, error correction, calibration, and/or quality control or assurance.

Generally, fusion of signals or sensor data from a plurality of devices allows:
- detection of a false positive or false negative signal from a first device with a second device;
- noise recognized in data from a first sensor type as the noise is not present in a second sensor type;
- fusion of environmental data with medical data;
- determination of an additional parameter not measured or independently measured with individual data types of the fused data;
- electrocardiograph data to aid in analysis of photoplethysmograph data and vise-versa; and/or
- electrodynamic information to aid in analysis of hemodynamic information and vise-versa.

Hardware

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data and where the input data includes at least one of: a photoplethysmogram and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

More generally, the probabilistic digital signal processor is a physical processor, is integrated into a processor, such as in a computer, and/or is integrated into an analyzer. The analyzer is a physical device used to process data, such as sensor data 122. Optionally, the analyzer includes an input device, a power supply, a central processing unit, a memory storage unit, an output display screen, a communication port, and/or a wireless connector. Preferably, the analyzer is integrated with a sensor, such as integrated into any of:
- a pulse oximeter;
- an electrocardiogram device;
- a biomedical device;
- a medical rack system;
- a mechanical sensing system;
- a complex machine;
- a car;
- a plane;
- a fluid monitoring system; and/or
- an oil transport line.

Optionally, the analyzer is configured to receive information from one or more sensors or instruments. Generally, the analyzer is configured for signal processing, filtering data, monitoring a parameter, generating a metric, estimating a parameter value, determining a parameter value, quality control, and/or quality assurance.

Additional Embodiments

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, supra, to describe the use of the probabilistic model approach. However, the probabilistic model approach is more widely applicable.

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data, and where the input data comprises at least one of: a photoplethysmogram and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, infra, to describe the use of the probabilistic model approach. However, the probabilistic model approach is more widely applicable.

Some examples of physiological sensors used for input into the system with a corresponding physiological model include:
- an ECG having about two to twelve leads yielding an ECG waveform used to determine an RR-interval and/or various morphological features related to arrhythmias;
- pulse photoplethysmography yielding a PPG waveform for determination of hemoglobins and/or total hemoglobin;
- a multi-wavelength model;
- capnography or IR absorption yielding a real time waveform for carbon dioxide determination, end-tidal $CO_2$, an inspired minimum, and/or respiration rate;
- a temperature sensor for continuous determination of core body temperature and/or skin temperature;
- an anesthetic gas sensor including nitrous oxide, $N_2O$, and carbon dioxide, $CO_2$, used to determine minimum alveolar concentration of an inhaled anesthetic;
- a heart catheter yielding a thermodilution curve for determination of a cardiac index and/or a blood temperature;
- an impedance cardiography sensor yielding a thoracic electrical bioimpedance reading for determination of thoracic fluid content, accelerated cardiac index, stroke volume, cardiac output, and/or systemic vascular resistance;
- a mixed venous oxygen saturation catheter for determination of $SvO_2$;
- an electroencephalogram (EEG) yielding an EEG waveform and characteristics thereof, such as spectral edge frequency, mean dominant frequency, peak power frequency, compressed spectral array analysis, color pattern display, and/or delta-theta-alpha-beta band powers, any of which are used for analysis of cardiac functions described herein;

electromyography (EMG) yielding an EMG waveform including frequency measures, event detection, and/or amplitude of contraction;

auscultation yielding sound pressure waveforms;

transcutaneous blood gas sensors for determination of carbon dioxide, $CO_2$, and oxygen, $O_2$;

a pressure cuff yielding a pressure waveform for determination of systolic pressure, diastolic pressure, mean arterial pressure, heart rate, and/or hemodynamics;

spirometry combining capnography and flow waveforms for information on respiratory rate, tidal volume, minute volume, positive end-expiratory pressure, peak inspiratory pressure, dynamic compliance, and/or airway resistance;

fetal and/or maternal sensors, such as ECG and sound (auscultatory) sensors for determination of fetal movement, heart rate, uterine activity, and/or maternal ECG;

laser Doppler flowmetry yielding a velocity waveform for capillary blood flow rate;

an ultrasound and/or Doppler ultrasound yielding a waveform, such as a two-dimensional or three-dimensional image, for imaging and/or analysis of occlusion of blood vessel walls, blood flow velocity profile, and/or other body site dependent measures;

a perspirometer yielding a continuous or semi-continuous surface impedance for information on skin perspiration levels; and/or a digital medical history database to calibrate the model or to screen the database for patient diseases and/or conditions.

Some examples of non-physiological sensors used for input into the system with a corresponding physiological model include:

an accelerometer;

a three axes accelerometer;

a gyroscope;

a compass;

light or a light reading;

a global positioning system, for air pressure data, ambient light, humidity, and/or temperature;

a microphone; and/or an ambient temperature sensor.

While specific dynamic state-space models and input and output parameters are provided for the purpose of describing the present method, the present invention is not limited to examples of the dynamic state-space models, sensors, biological monitoring devices, inputs, and/or outputs provided herein.

Diagnosis/Prognosis

Figure 19:
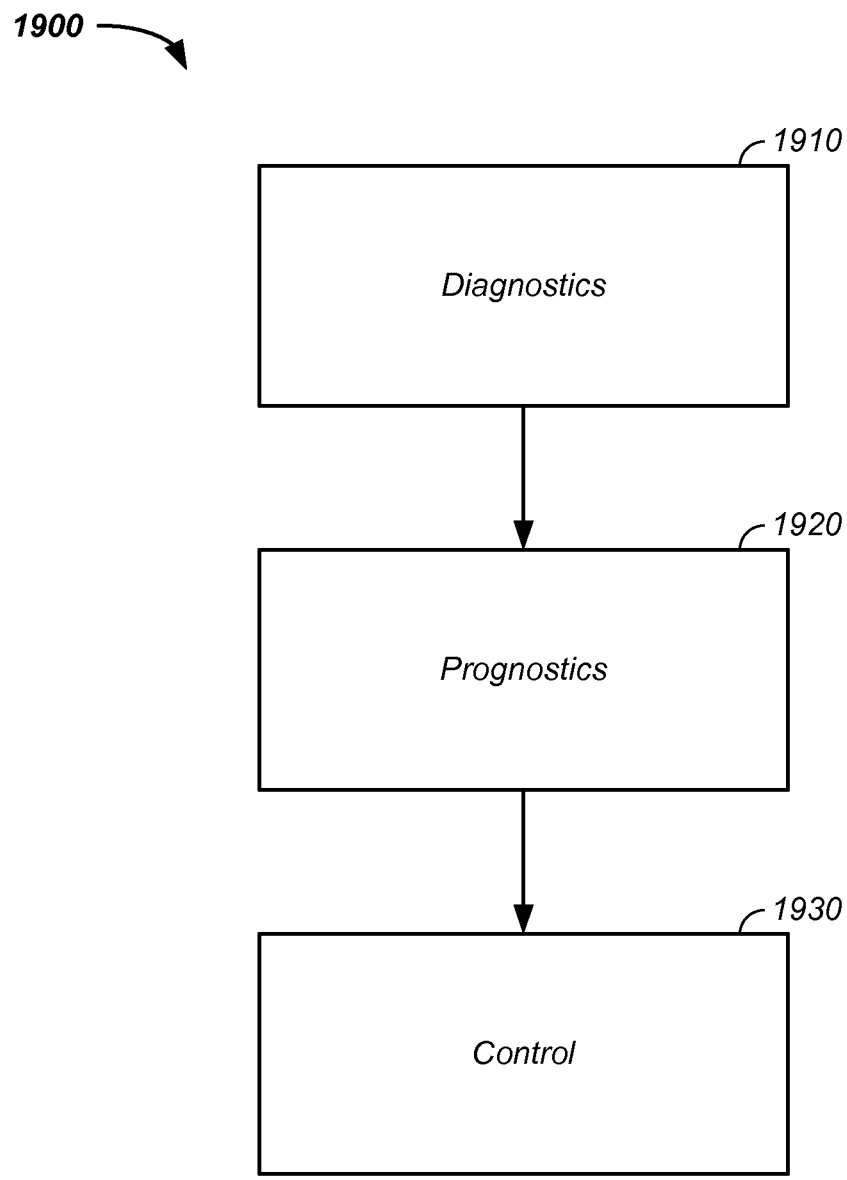
FIG. 19 provides a flowchart of dynamic state-space model diagnostics used as prognosis and control.

Referring now to FIG. 19, the output of the probabilistic digital signal processor 200 optionally is used to diagnose 1910 a system element or component. The diagnosis 1910 is optionally used in a process of prognosis 1920 and/or in control 1930 of the system.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for processing sensor data representative of a body, comprising the steps of:
   using a physical model, representative of function of a body constituent, coded into a digital signal processor of an analyzer, wherein said physical model comprises the step of:
   using a fitting constant related to at least one of age and gender;
   generating a prior probability distribution function using said physical model;
   repetitively fusing input data originating from at least a first medical instrument and a second medical instrument with the prior probability distribution function to generate a posterior probability distribution function; and
   processing the posterior probability distribution function with said processor to generate an output of least one of:
   a heart attack prediction; and
   a heart stroke volume, wherein said step of processing uses at least one equation relating heart stroke volume to the posterior probability distribution function.

2. The method of claim 1, further comprising the steps of:
   determining a noise artifact event through analysis of the input data from said first instrument; and
   using said noise artifact event to filter the input data from said second instrument.

3. The method of claim 1, wherein said estimated parameter value comprises:
   a metric to a parameter not output by either said first instrument or said second instrument.

4. The method of claim 3, wherein said metric comprises a permittivity.

5. The method of claim 1, wherein the input data from said first instrument comprises hemodynamic data outside of a heart of the body.

6. The method of claim 5, wherein the input data from said second instrument comprises electrodynamic data representative of an electrodynamic signal originating in the heart of the body.

7. The method of claim 6, further comprising the step of:
   using both the hemodynamic data and the electrodynamic signal to generate an estimate of the autonomic nervous system tone.

8. The method of claim 2, further comprising the step of:
   combining the input signal from said first instrument and said second instrument, said step of combining resulting in at least one of:
   a generated measure of heart rate; and
   a heart rate variability measure,
   wherein the input data from said first instrument comprises a hemodynamic measure.

* * * * *